(12) United States Patent
Selden

(10) Patent No.: US 7,094,400 B1
(45) Date of Patent: *Aug. 22, 2006

(54) TRANSKARYOTIC IMPLANTATION

(75) Inventor: Richard F. Selden, Cambridge, MA (US)

(73) Assignee: Shire Human Genetic Therapies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/465,596

(22) Filed: Jun. 5, 1995

Related U.S. Application Data

(63) Continuation of application No. 08/312,444, filed on Sep. 26, 1994, now abandoned, which is a continuation of application No. 08/180,701, filed on Jan. 13, 1994, which is a continuation of application No. 07/918,927, filed on Jul. 22, 1992, which is a continuation of application No. 07/787,760, filed on Nov. 6, 1991, which is a continuation of application No. 07/044,719, filed on May 1, 1987.

(51) Int. Cl.
*A01N 63/00* (2006.01)
*A61K 48/00* (2006.01)
*C12N 15/00* (2006.01)

(52) U.S. Cl. ............... 424/93.21; 424/93.2; 435/320.1; 435/455

(58) Field of Classification Search ............... 424/93.1, 424/93.2, 93.21; 435/240.2, 320.1, 172.3, 435/172.1, 325, 326, 248, 349, 350, 351, 435/352, 353, 354, 355, 356–372.3, 466, 435/455; 536/23.1, 23.5, 23.2; 514/44
See application file for complete search history.

(56) References Cited

U.S. PATENT DOCUMENTS

| | | | | |
|---|---|---|---|---|
| RE30,059 E | * | 7/1979 | Lindstrom | 436/536 |
| 4,332,893 A | * | 6/1982 | Rosenberg | 435/70.3 |
| 4,497,796 A | * | 2/1985 | Salser et al. | 514/44 |
| 4,621,050 A | * | 11/1986 | Sugimoto | 435/70.2 |
| 4,621,053 A | * | 11/1986 | Sugimoto | |
| 4,897,355 A | | 1/1990 | Eppstein et al. | 435/172.3 |
| 4,946,787 A | | 8/1990 | Eppstein et al. | 264/4.1 |
| 5,049,386 A | | 9/1991 | Eppstein et al. | 424/427 |
| 5,208,036 A | | 5/1993 | Eppstein et al. | 424/450 |
| 5,366,737 A | | 11/1994 | Eppstein et al. | 424/450 |
| 5,622,712 A | | 4/1997 | Eppstein et al. | 424/450 |
| 5,994,127 A | * | 11/1999 | Selden | 435/325 |
| 6,048,524 A | * | 4/2000 | Selden | 435/325 |
| 6,048,729 A | * | 4/2000 | Selden | 435/455 |
| 6,054,288 A | * | 4/2000 | Selden | 435/69.1 |
| 6,187,305 B1 | * | 2/2001 | Treco | 435/69.1 |
| 6,303,379 B1 | * | 10/2001 | Selden | 435/455 |
| 6,355,241 B1 | * | 3/2002 | Selden | 424/93.2 |

FOREIGN PATENT DOCUMENTS

EP    0 161 640    * 11/1985

OTHER PUBLICATIONS

Baker et al., 1982, in: Fourth Edition, The Study of Biology, Addison-Wesley Publishing Co., Menlo Park, CA, p. 922.*
Cline, 1987, Am. J. Med. 83, 291-297.*
Selden et al., 1987, New Eng. J. Med. 317(17), 1067-1076.*
Goding, 1983, in: Monoclonal Antibodies: Principles and Practice, Academic Press, London, pp. 87-88.*
Williams et al., 1984, Nature 310, 476-480.*
Miller et al., 1984, Science 225, 630-632.*
Anderson, 1984, Science 226, 401-408.*
Sevier et al., 1981, Clinical Chemistry 27(11), 1797-1806.*
Crystal, 1995, Science 270, 404-410.*
Robinson, C., 1993, TIBTECH 11, 155.*
Orkin et al., Dec. 7, 1995, "Report and Recommendations of the Panel to Assess the NIH Investment in Research on Gene Therapy".*
Selden et al., (1986) Molec. Cell. Biol. 6(9): 3173-3179.*
Vieira et al., (1981) Gene 19: 259-268.*
Lindahl et al. Cellular Aspects of Gene Therapy. Growth Factors in Health and Disease. Elsevier Science Publishers B.V. (Biomedical Division, Westermark, C. et al. eds. 1990, pp. 383-392.*
Greenhalgh et al. Epidermis: An Attractive Target Tissue For Gene Therapy. Journal Invest. Dermatol. 1994, Bol. 103, pp. 63S-69S.*
Ghazizadeh et al. Virus-Mediated Gene Transfer for Cutaneous Gene Therapy. Human Gene Therapy. Nov. 1, 2000, vol. 11, pp. 2247-2251.*
Mulligan R. The Basic Science of Gene Therapy. Science. May 14, 1993, vol. 260, pp. 926-932.*

* cited by examiner

*Primary Examiner*—Deborah Crouch
(74) *Attorney, Agent, or Firm*—Wolf, Greenfield & Sacks, P.C.

(57) ABSTRACT

The present invention provides a method of altering the concentration or level of expression of a desired gene product in a recipient subject which involves administering to a recipient a transkaryotic cell capable of expressing a desired gene when the cell is present within the subject. The invention further pertains to compounds produced by such cells, by transkaryotic animals in response to such cells, and to the uses of such compounds.

15 Claims, 9 Drawing Sheets

TRANSKARYOTIC IMPLANTATION

This application is a continuation of application Ser. No. 08/312,444 filed Sep. 26, 1994, now abandoned, which is a File Wrapper Continuation of Ser. No. 08/180,701, filed Jan. 13, 1994, which is a File Wrapper Continuation of Ser. No. 07/918,927, filed Jul. 22, 1992, which is a File Wrapper Continuation of Ser. No. 07/787,760, filed Nov. 6, 1991, which is a File Wrapper Continuation of Ser. No. 07/044,719, filed May 1, 1987.

FIELD OF THE INVENTION

This invention relates to a technique for altering the level of gene expression which involves the introduction of a genetically engineered cell into a recipient individual. The invention further relates to compounds, especially antibodies, produced by such cells, and to the uses of such compounds.

BACKGROUND ART

Diseases which are inherited from an individual's parents are known as genetic diseases. At least 1,500 distinguishable human diseases are already known to be genetically determined (McKusick, V. A., Mendelian Inheritance in Man (Johns Hopkins Press, Baltimore, 3rd. Ed., 1971). The specific molecular basis for most of these diseases is not yet understood; however, in many cases the basis of the disease has been determined to be a specific enzyme deficiency (McKusick, V. A., Ann Rev. Genet. 4:1 (1970)).

At present, no wholly acceptable method of gene therapy is known. Human genetic diseases are usually treated either by dietary therapy (such as the avoidance of phenylalanine by individuals who suffer from phenylketonuria), by drug therapy (such as the use of inhibitors of the enzyme xanthine oxidase (i.e., allopurinol), to reduce the accumulation of uric acid associated with gout and Lesch-Nyhan syndrome), or through gene product replacement therapy (such as by administering factor VIII to individuals who suffer from hemophilia).

Unfortunately, many genetic diseases do not yet respond to any of the above treatments. For example, genetic disorders of amino acid metabolism cannot generally be well controlled by dietary therapy. Storage diseases associated with lysosomal enzyme deficiencies have not thus far been found to respond to enzyme therapy. In addition, even where a disease may be controlled through any of the above methods, disease management is seldom perfect.

In response to the deficiencies of the above techniques, investigators have attempted to apply recombinant DNA technology to the treatment of genetic diseases. Such gene therapy can be broadly defined as a medical/surgical intervention in which the genome of the patient is purposely altered to ameliorate a pathophysiologic condition, and as such the term can be sub-divided into germ line and somatic cell gene therapy. Based on both ethical and practical criteria, it is not feasible to attempt germ-line gene therapy on human subjects. From an ethical perspective, modifying the germ line would change, albeit slightly, subsequent generations of humans, with the longterm effects not entirely predictable. Somatic cell gene therapy, in contrast, would only affect the individual subjected to the therapy, and the new gene would not enter the gene pool. From a practical perspective, germ line gene transfer is relatively inefficient, the fate of the injected genes cannot be predicted, and, perhaps most importantly, with few exception it would not be possible to determine the future phenotype (with respect to a given disease) of a single cell or early cleavage embryo.

Somatic cell gene therapy, however, does seem to be a reasonable approach to the treatment and cure of certain disorders in human beings. In a somatic cell gene delivery system, cells from the patient are removed, cultured in vitro, transfected, and reimplanted. Modifications of this basic scheme include, but are not limited to, choices of the cell type and cell donor (not necessarily the patient), the transfection protocol, and the site of reimplantation.

Several techniques have thus far been developed which offer promise as means for delivering DNA into an individual. A well-described technique involves retroviral vectors (Varmus, H., et al., in: RNA Tumor Viruses, Weiss et al., Eds. (Cold Spring Harbor Laboratory, New York, 1982); Varmus, H., Science 216:812 (1982); Risser, R., et al., Ann. Rev. Genet. 17:85 (1983)). In this approach, a particular gene is inserted into a retrovirus which is then introduced into an individual. Retroviruses store their genetic information in RNA, and, on entering a cell, reverse transcribe (hence the name "retro") this information into DNA, which can then become integrated and expressed in the host cell's genome. In practice, a recombinant retrovirus containing the gene of interest and a portion of the retroviral genome (some retroviral genes are removed so that the virus cannot replicate) is constructed using genetic engineering methodologies. This artificial virus is utilized to infect marrow cells in vitro, and these cells are injected intravenously into lethally irradiated recipient mice, where they ultimately make their way to the marrow and spleen. Using this approach, genes encoding neomycin phosphotransferase (Williams, D. A., et al., Nature, 310:476–481 (1984)), adenosine deaminase (Williams, D. A., et al., Proc. Natl. Acad. Sc. USA, 83:2566–2570 (1986)), and hypoxanthine phosphoribosyltransferase (Miller, A. D. et al., Science 225:630–632 (1984)) have been expressed in mice.

In the past few years, it has become apparent that the implementation of retroviral based gene delivery systems in humans will face major obstacles, primarily related to properties of retroviruses themselves (Robertson, M., Nature 320:213–214 (1986), Marx, J. L., Science 232:824–825 (1986)). First, it has not been generally possible to achieve expression of mammalian genes in the retroviral vectors used to infect human cells, and until this problem is solved, the issue of regulated gene expression cannot be addressed. Second, when retroviruses are used to infect marrow cells in batch, essentially every cell is infected, and the site of retroviral integration into the host's genome varies from cell to cell. Since the infected cells are not characterized before reintroduction, the possibility of a deleterious intergration event cannot be eliminated. Third, as recombination between the replication-deficient retroviruses utilized for the infection and the endogenous retroviruses present in mammalian genomes is known to occur (Hock, R. A. et al., Nature 320:275–277 (1986)), there is the potential of initiating a chronic retroviral infection in the host animal. Fourth, marrow is probably not the optimal site of expression for many (if not most) genes of therapeutic import.

An alternative approach for gene therapy involves introducing DNA into a cell by chemical, as opposed to viral, techniques. In this approach, DNA is introduced into a recipient call by calcium phosphate-mediated transfection. In general, the recipient cells are first removed from an individual and incubated in the presence of a DNA solution containing the gene whose introduction is desired. After the gene has been introduced into the cell, the cell is returned to the individual. At present, the only cells which may be removed from an individual, treated, and subsequently reintroduced are bone marrow stem cells and skin fibroblasts (Anderson, W. F., *Science* 226:401–409 (1984)). Cline, M. J., et al. (*Nature* 284:422 (1982)) disclosed the successful transfer of a functional dihydrofolate reductase gene into the bone marrow of mice.

Present chemical techniques suffer from substantial drawback of low efficiency. Transfection has been found to occur in only one of $10^6$ or $10^7$ cells. Thus, since only approximately $10^7$ or $10^8$ cells may be routinely obtained from an individual by bone marrow transplantation, the chemical technique would mean that 10 to 100 stem cells would be transfected. In addition, the difficulty of culturing such cells for more than a few days is a substantial limitation to this method. It is currently believed that the presence of so few modified cells, when compared to the total number of cells in the bone marrow population, would have little therapeutic value.

A third major current approach to gene therapy involves the use of physical techniques such as micro-injection or electroporation. Microinjection involves the injection of DNA into isolated, individual cells. The technique, though extremely efficient, suffers from the disadvantage that only one cell at a time can be injected. This technique has been most successful in the introduction of DNA into fertilized mouse eggs (Gordon, J. W., et al., *Science* 214:1244 (1981); Wagner, E. F., et al., *Proc. Natl. Acad. Sci. USA* 78:5016 (1981); Wagner, T. E., et al., *Proc. Natl. Acad. Sci. USA* 78:6376 (1981); Palmiter, R. D., et al., *Nature* 300:611 (1982)). Hammer, R. E., et al., (*Nature* 311:65 (1984)), used this technique to partially correct a mouse with a defect in its growth hormone production. Electroporation involves the transport of DNA directly across a cell membrane through the use of an electric current. It has been used to transfer DNA into B lymphocytes (Neumann, E., et al., *EMBO J.* 1:841 (1982)).

In summary, various conventional and recombinant techniques have been proposed for the treatment of genetic diseases. At present, however, no single technique appears to be wholly satisfactory. The use of viral vectors suffers from their potential for rearrangement of endogenous genes, as well as their potential for inducing carcinogenesis. Physical techniques, though highly efficient, are at present incapable of application to the large numbers of cells which would need to be transfected in order to provide a reasonable therapy. Chemical procedures involve the introduction of DNA into a cell which had previously been extracted from a subject individual. At present, the technique is limited to bone marrow cells and fibroblasts, and is not efficient enough to constitute a viable therapy. The state of this field is reviewed by Friedman, T., et al. (*Science* 175:949–955) (1972) and Anderson, W. F. (*Science* 226:401–409 (1984)).

Binding proteins, such as antibodies, are widely used to assay for the presence or concentration of particular molecules, such as antigens or haptens. An antigen is a molecule which, when introduced into an animal, provokes the animal to produce antibodies which are capable of binding to it. In contrast, a hapten molecule is capable of binding to antibodies, but is incapable of eliciting their production. Antibodies bind to both haptens and antigens by identifying particular structural regions (known as "epitopes") of the molecules. A hapten or antigen molecule may contain more than one epitope region.

Preparations of antibodies may be broadly divided into two classes. Polyclonal antibody preparations are obtained by injecting (or otherwise presenting) an antigen molecule into an animal. The presence of the antigen molecule stimulates antibody-producing cells to produce species of antibodies capable of binding to the epitopes of the antigen. Different antibody-producing cells are capable of producing different antibody molecules. Thus, the introduction of an antigen into an animal results in the production of an array of different antibody molecules which includes antibodies capable of binding to each of the epitopes of the antigen molecule. Because such a preparation includes antibodies which were produced from different producer cells, it is termed a "polyclonal" antibody preparation.

Excellent reviews of the methods and techniques for preparing polyclonal antibodies can be found in *Microbiology*, 2nd Edition; Davis, B. D., et al.; Harper & Row, New York (1973), pp. 352–358; and *Remington's Pharmaceutical Sciences*, 16th Edition, Osol, A., Ed., Mack Publishing, Easton, Pa. (1980), pp. 1315–1351.

The fact that individual antibody-producing cells are capable of producing only a single species of antibody is highly significant. Such individual cells can be clonally purified and fused to immortalized myeloma cells, thereby producing an immortalized cell which is capable of producing a single antibody species. Such fusion cells are known as "hybridoma" cells, and the antibodies which they produce are known as "monoclonal" antibodies. The procedures for producing monoclonal antibodies are disclosed in U.S. Pat. No. 4,172,124 (Koprowski, H., et al.) and in *Monoclonal Antibodies, Hybridomas: A New Dimension in Biological Analyses*, Kennett, R. H., et al. (Eds.), Plenum Press, NY (1980).

The distinction between monoclonal and polyclonal antibodies does not lie in their individual specificity or binding affinity. Both types of antibody molecules exhibit equivalent specificity and binding affinity toward antigen molecules. Preparations of polyclonal antibodies comprise either an unfractionated mixture, or purified mixtures of IgG molecules, of different antibody species, many of which are capable of binding to different epitopes. In contrast, a preparation of monoclonal antibodies contains only a single antibody species. Because they are composed of a single species, preparations of monoclonal antibodies (though not necessarily the antibodies themselves) may possess greater specificity than can a preparation of polyclonal antibodies.

Significantly, in order to produce either monoclonal or polyclonal antibodies, it is generally necessary for one to present substantial amounts of the antigen to the antibody-producing cells. Thus, in general, it is necessary to isolate and purify the antigen molecules before antibody production can be induced. In practice, however, it is often difficult to isolate and purify particular antigen molecules. This is especially true if the antigen molecules are hormones, membrane proteins, or other molecules which are present at only very low concentrations in source materials. Thus, for such molecules, it is often difficult or not possible to obtain antibodies. Hence, a need exists for a method of producing antibodies which does not require the prior isolation or purification of the antigen molecule.

SUMMARY OF THE INVENTION

The present invention provides a method of altering the concentration of a desired gene product in a recipient subject. The invention also provides a means for compensating for a possible defect in the subject's expression of a particular gene, or for providing a means for increasing or decreasing the subject's expression of a particular gene.

In detail, the invention provides a method of altering the concentration of a desired gene product in a recipient subject which comprises providing to the recipient subject a transfected cell preparation, the preparation containing at least one transfected cell which contains a desired gene sequence, wherein the cell, when provided to the subject, will direct the expression of the desired gene sequence, thereby causing the production of a desired gene product.

The invention also provides a method of altering the concentration of a desired gene product in a recipient subject which comprises providing to the recipient subject a transfected cell preparation, the preparation containing at least one transfected cell which contains an effector gene sequence, wherein the cell, when provided to the subject, will direct the expression of the effector gene sequence, thereby causing the production of a desired gene product.

The invention further pertains to a method for inducing the production of a biological compound which comprises providing to a recipient subject an effective amount of a transfected cell preparation, the preparation containing at least one transfected cell which contains a desired gene sequence, wherein the cell, when provided to the subject, will direct the expression of the desired gene sequence, thereby causing the production of a desired gene product (I); the expression of the desired gene sequence being sufficient to induce a non-transfected cell of the recipient subject to produce the biological compound.

The invention additionally pertains to a method for determining the concentration of a desired gene product (II) in a sample which comprises:

(a) incubating the sample in the presence of a biological compound capable of binding the desired gene product (II), the production of the biological compound being induced by a method which comprises providing to a recipient subject an effective amount of a transfected cell preparation, the preparation containing at least one transfected cell which contains a desired gene sequence, wherein the cell, when provided to the subject, will direct the expression of the desired gene sequence, thereby causing the production of a desired gene product (I); the expression of the desired gene sequence being sufficient to induce a non-transfected cell of the recipient subject to produce the biological compound, (b) determining the concentration of the desired gene sequence by measuring the amount of the biological molecule bound to the desired gene product (II).

The invention also includes a method for determining the concentration of a desired gene product (II) in a sample which comprises:

(a) incubating the sample in the presence of two different biological compounds capable of binding the desired gene product (II), the production of at least one of the biological compounds being induced by a method which comprises providing to a recipient subject an effective amount of a transfected cell preparation, the preparation containing at least one transfected cell which contains a desired gene sequence, wherein the cell, when provided to the subject, will direct the expression of the desired gene sequence, thereby causing the production of a desired gene product (I); the expression of the desired gene sequence being sufficient to induce a non-transfected cell of the recipient subject to produce the biological compound, (b) determining the concentration of the desired gene product (II) by measuring the amount of the biological compounds bound to the desired gene product (II).

The invention also includes a method for evaluating an agent suspected of having immunosuppressive activity which comprises (a) introducing a transfected cell preparation which expresses an antigen into a recipient subject, (b) administering the agent to be evaluated to the recipient subject, and (c) determining whether the administration of the agent affected the ability of the recipient subject to produce antibodies capable of binding to the antigen.

The invention also includes an implant which comprises a transfected cell.

DESCRIPTION OF THE PREFERRED EMBODIMENT

The compositions and methods of the present invention can be used in two different manners. In the first embodiment, the purpose of the compositions and methods is to provide gene therapy to a recipient subject. In the second embodiment the purpose of the compositions and methods is to induce the recipient subject to produce a specific biological compound in response to the presence of compounds produced by a transfected cell.

I. Terminology of the Invention.

Figure 1:
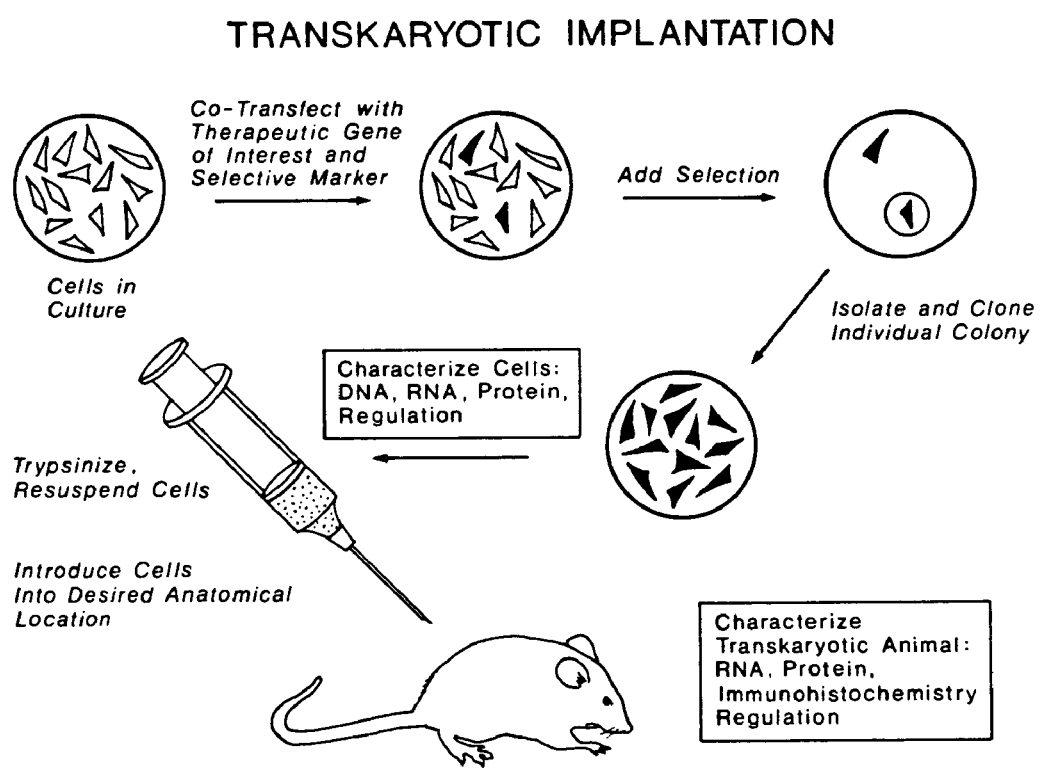
FIG. 1 shows a diagramatic representation of one embodiment of transkaryotic implantation. Cultured cells are co-transfected with the gene of therapeutic interest and a gene encoding a selectable marker. Stably transfected cells are identified by their ability to express the marker gene as evidenced by their ability to survive the selection regimen (cells that have not taken up the marker gene are destroyed by this regimen). Invididuals colonies of stably transfected cells are then multiplied and characterized with respect to the expression and regulation of the gene of therapeutic interest. A clonal line possessing the desired expression properties is then introduced into one of a variety of anatomical locations in the host animal, which is itself characterized with respect to expression of the gene of interest.

The present invention provides a novel method for accomplishing the alteration of the concentration of a desired gene product in a recipient subject. This alteration involves the introduction of a transfected cell which carries either a desired gene sequence or an effector gene sequence into the recipient subject. To be used in accord of the present invention the introduced desired gene sequence must be capable of being expressed in the recipient subject. FIG. 1 shows a schematic diagram of transkaryotic implantation.

The "subject recipient" with which the present invention may be employed include animals, as well as humans; and the term "subject recipient" as used herein is meant to refer to the recipient of the transfected cell containing the desired gene.

According to the present invention, a "transfected cell" is a cell which has been manipulated in vitro so that it contains a particular gene whose expression in a recipient subject is desired. Thus, for example, if it is desired to express the growth hormone gene in a particular subject, then one would introduce the gene for growth hormone into a cell (thereby forming a transfected cell) in such a manner that the cell would express this gene when introduced into the recipient subject. Typically, although not necessarily, this gene sequence will be identical to the normal gene sequence of the species to which the recipient subject belongs. Thus, if one desired to provide additional growth hormone to an animal, one could employ a transfected cell which contained either that animal's growth hormone gene or, alternatively, the hormone gene of a different species as long as the growth hormone gene employed would be capable of expression in the recipient subject.

A recipient subject which contains such a transfected cell is said to be a "transkaryotic" recipient subject. A transkaryotic animal differs substantially from a transgenic animal. In a transgenic animal, all of the animal's cells contain a gene sequence which is not naturally present in other animals of the same species. In a transkaryotic animal, only the introduced transfected cells contain such a sequence; the vast preponderance of cells of the animal are unaltered. Thus, transgenic therapy involves altering an animal's germ line in a manner which changes the genetic content of each of the animal's cells. In contrast, transkaryotic therapy involves somatic cells and does not alter the genetic content of the animal's cells.

The introduction of a transfected cell into a recipient subject is herein referred to as "transkaryotic implantation."

A "transfected cell preparation" is a suspension of cells, which contains at least one transfected cell, either (1) in a physiologically acceptable buffer or carrier or (2) within a physiologically acceptable container. Phosphate-buffered saline is an example of such a suitable carrier. A "transkaryotic implant" is an implant which contains at least one transfected cell.

II. The Expression of Transfected Cells in a Recipient Subject

The present invention provides a means of providing gene therapy to a recipient subject. Such therapy is provided through the introduction of a transfected cell (capable of expressing a particular gene sequence into the subject). The specific sequence, or nature of the genetic sequence to be introduced into the subject will be chosen depending upon the specific gene product whose concentration in the recipient subject one wishes to alter. The introduced gene sequence may alter the concentration of the desired gene product by being capable of expressing the desired gene product (or an equivalent or mutant form of the desired gene product) in which case the introduced gene sequence is termed a "desired gene sequence." The introduced gene sequence may alternatively alter the concentration of the desired gene product by effecting the expression of the desired gene product by the non-transfected (i.e., native) cells of the recipient subject, in which case the gene sequence is termed an "effector gene sequence." Thus, if one wished to alter the concentration of growth hormone, one could introduce genetic sequences capable of directly effecting the concentration of the growth hormone by providing a transfected cell which expresses growth hormone or indirectly by inducing the expression of growth hormone by a non-transfected cell of the animal. In a similar manner, any gene which can be isolated and cloned may be used in accord of the present invention.

The term "expression" as used herein refers to the ability of a cell to direct the transcription of a genetic sequence into mRNA, the translation of the mRNA into protein and the secretion of the protein out of the cell. Secretion of gene products may occur naturally or may be obtained by operably linking the desired or effector gene to a secretory signal sequence. Expression is said to be "normal" if it occurs at a level within accepted norms for that particular gene product in a particular species, or if the level of expression is essentially equivalent to that observed in untreated subjects of the same species as the recipient subject. "Non-normal expression" typically refers to expression which is less than that found in normal members of the subject's species, although it may also describe the overexpression of a particular gene product. Expression is considered to be "physiologically significant" if it results in a change in the physiology of the recipient subject. Thus, expression which is of so low a level as to not have any physiological import to the recipient subject would not be considered to be physiologically significant. Conversely, if expression effects the gross physiology of a recipient subject, it is physiologically significant, as that term is used herein.

In order to accomplish gene expression, it is necessary that the structural sequences of the desired of effector gene be operably linked to a promoter region. A promoter region is a DNA sequence recognized by the transfected cell as a site at which to commence the transcription of a gene sequence. A gene sequence is said to be operably linked to a promoter region if the linkage is sufficient to enable the gene sequences to be transcribed due to the presence of the promoter region. In one embodiment of the present invention, the desired or effector DNA sequences are introduced into the transfected cell linked to their normal and natural promoter regions. Such transfected cells are capable of producing the product of the desired or effector gene under that gene's normal regulatory control. Alternatively, in a preferred embodiment, it is possible to link a particular desired or effector gene sequence to a promoter region with which it is not normally associated. Thus, any promoter capable of functioning in the transfected cell can be operably linked to the desired or effector gene sequence and used to express the gene in the transkaryotic cell.

The promoter region may either be constitutive (i.e., continually capable of expressing a gene only in response to certain conditions and being otherwise substantially incapable of promoting such expression). Among the preferred regulatable promoter regions which may be employed is the mouse metallothionein promoter region. This promoter region directs transcription of operably linked genetic sequences in direct response to the concentration of certain heavy metals (i.e., zinc or cadmium) or glucocorticoids. Thus, by administering such ions to the recipient subject, one can control the level of expression of the operably linked gene sequences.

Alternatively, promoter regions which are regulatable by temperature (such as the Drosophila heat shock promoter), sugars (such as the yeast gal-4 promoter), double-stranded RNA, etc., may be employed.

The utility of gene therapy extends beyond the treatment of classic genetic disorders, those heritable diseases caused by a missing or mutant gene which results in an absent or aberrant protein product. A variety of pathophysiologic conditions can be treated by the delivery of a specific protein, exemplified by the application of gene therapy to diabetes. Although both Types I and II diabetes may have a genetic component, in the vast majority of cases the insulin gene itself is unaffected. Also in this category fall various temporary interventions that are not geared towards the replacement of a defective gene. For example, tissue plasminogen activator, which is quite difficult to produce in large quantities, is currently being evaluated for treatment of patients who have suffered recent myocardial infarctions. Cells taken from such a patient could be engineered to express tissue plasminogen activator and reimplanted, reducing the possibility of subsequent life-threatening clot formation. Similarly, transkaryotic implantation may be utilized to deliver a product designed to destroy certain malignancies. Transkaryotic implantation may be used to provide temporary therapy to trauma or burn victims.

Several features are desirable in a gene therapy which employs transkaryotic implantation: I) The transfected cells should be fully characterized before implantation into the patient; II) The gene(s) should be delivered efficiently and the desired level of regulated expression achieved; III) It should be possible to utilize cells derived from different tissues for transfection and to reimplant them into different anatomical locations depending upon clinical considerations; IV) It should be possible to detect, monitor, and perhaps modulate the function of the transfected cells post-implantation; V) The implanted cells should be engineered so that they can be completely destroyed or inactivated, if necessary, at any time after implantation; VI) The system must have clear therapeutic benefits and must not subject the patient or the population to undue risk. As indicated above, this alteration may provide to a recipient subject a new gene which had not previously been present in the recipient subject's genome. In such a case, the recipient subject would, for the first time, be capable of expressing the introduced gene sequence. Alternatively, the present invention provides a means for increasing the level of gene expression in the recipient subject.

III. Use of Transkaryotic Implantation to Provide Gene Therapy

The present invention provides a means for altering the level of gene expression in a subject recipient. This alteration may either increase or decrease gene expression.

Gene expression may be increased by providing to the subject recipient a transfected cell which contains a gene substantially identical or equivalent to that gene of the recipient subject whose amplified expression is desired. The expression of such a gene by the transfected cell thereby causes an increase in the concentration of the desired gene product in the recipient subject. As used above, an "equivalent gene" is a gene similar to that of the recipient subject, but derived from a different species. For example, the gene for bovine growth hormone would be equivalent to the human growth hormone gene. An "identical gene" is a gene which is substantially similar to the gene sequence normally and naturally present in the recipient subject. An "equivalent" or "identical" gene sequence may be either a "desired gene sequence" or "an effector gene sequence."

It is possible to increase gene expression in accordance with the present invention by providing to the recipient subject a transfected cell which contains an "effector gene sequence" (i.e., one which effects the regulation of a gene whose increased expression is desired). Thus, for example, the level of expression of a particular gene in a recipient subject may be increased by providing to that subject a transfected cell which expresses a gene whose product stimulates the endogenous expression of a second, desired gene sequence in the recipient subject. For example, gene expression could be increased by providing to a recipient subject, a transfected cell which expressed a gene whose product induced the subject to secrete elevated levels of growth hormone.

The present invention may also be used to decrease the level of gene expression in the recipient subject. A decrease in gene expression may be obtained by providing to the recipient subject a transfected cell which expresses an effector gene sequence whose product represses the expression of an endogenous gene in the recipient subject. Thus, for example, by providing a transfected cell which expresses a gene whose product represses growth hormone expression (i.e., somatostatin), one could limit the amount of endogenous expression of the growth hormone gene in a recipient subject. Alternatively, one could obtain a decrease in gene expression by providing to the recipient subject a transfected cell which expressed a gene product which interfered with the normal activity or functioning of a particular gene. For example, the transfected cell might provide a gene product capable of complexing with a particular endogenous gene product, and thereby attenuate that gene product's activity.

An additional way of either increasing or decreasing gene expression in a recipient subject involves the use of a transfected cell to alter the physiologically significant concentration of the desired gene product in the recipient subject. Such a transfected cell may express a mutant allele of either (1) the gene whose expression one desires to alter, or (2) a gene whose expression effects the level of expression of the gene sequence of interest. Thus, for example, one means for increasing the level of expression of the growth hormone gene would be to provide to a recipient subject a transfected cell which expressed a mutant allele of the growth hormone gene capable of producing a mutant growth hormone having enhanced activity. Similarly, by providing a recipient subject with a transfected cell capable of producing a mutant human growth hormone product (having substantially impaired activity), one would decrease the number of growth hormone receptor molecules available to pair with the endogenous, normal growth hormone of the recipient subject. Such an occurrence would be essentially equivalent to decreasing the amount of endogenous growth hormone, and would result in a decrease in the physiological effect of the endogenous gene expression.

It is to be understood that the desired gene sequence present in the transfected cell may have been derived either from the recipient subject itself, from an animal of the same species as the recipient subject, from an animal of a different species, or it may be a synthetic gene. In choosing the source of the desired or effector gene sequence of the transfected cell, it is important to consider whether the expressed gene product of the transfected cell would be perceived as an antigen in the recipient subject. Thus, to avoid any possible immunological rejection of the expressed product of the transfected cell, it is desirable to obtain the desired or effector gene sequence from a species which is closely related to that of the subject individual and it is preferable to obtain this sequence from an animal of the same species as the receipient subject. It is most preferable to employ a gene sequence which was derived from the recipient subject itself. The possible antigenicity of the gene sequence expressed by the transkaryotic cell may be readily determined by ascertaining whether the sera of the recipient subject has, or can be primed to have, antibodies capable of specifically reacting with the expressed gene product. Techniques for determining the antigenicity of a protein are widely known by those of ordinary skill in the art.

IV. Use of Transkaryotic Implants to Induce the Production of Biological Compounds in a Recipient Subject One embodiment of the present invention involves the use of transfected cells to induce the production of a biological compound by the non-transfected cells normally present in a recipient subject. Examples of biological compounds which may be produced in accordance of this embodiment include antibodies, cellular receptor molecules, hormones, enzymes, etc. By implanting a particular transfected cell, capable of expressing an "effective amount" of a particular desired gene product, it is possible to induce the synthesis of a second particular gene product (by the non-transfected cells of the recipient subject). The term "effective amount" is intended to refer to an amount of expression which is physiologically significant. Thus, if an effective amount of a hormone gene is expressed in a recipient subject, then the level of hormone will be high enough to have a detectable effect on the physiology of the subject. If an effective amount of an antigenic substance is expressed in a subject recipient, then the level of the substance will be high enough to induce antibody production. Thus, for example, if the transfected cell expresses an antigen, then the recipient subject will be induced to produce antibodies capable of binding to it. Alternatively, if the transfected cell expresses a non-antigenic hormone or hormonal receptors, then the non-transfected cells of the subject recipient will be induced to produce hormonal receptor or hormone molecules through standard physiological mechanisms.

Importantly, the above-described embodiment of the present invention permits one to recover biological compounds produced in response to the presence of the expression product of the transfected cell without first having to purify the expression product molecule. At present, for example, high affinity, specific polyclonal antibodies can be produced only by providing substantial amounts of purified antigen. Often, because of the difficulty of purifying the antigen molecules, the production of polyclonal antibodies is an exceedingly difficult task. In contrast, it is frequently a simple matter to isolate a gene which encodes the antigen of interest. By introducing such a gene into a cell, it is possible to produce a transfected cell which expresses the antigen. This expression, in turn, leads to the production of antibodies by the subject recipient which are capable of specifically binding to the expressed antigen. Hence, the present invention provides a means for producing polyclonal antibodies which overcomes the existing requirement for purified antigen molecules.

Significantly, the expressed antigen need not be the production of an intact and entire gene. It may, alternatively, be the expression product of a "gene fragment." A "gene fragment" is a DNA sequence, which, when expressed, results in the production of a polypeptide which comprises only a fragment of an intact and entire gene. For example, if one desired to induce the production of antibodies capable of recognizing a hormone, it would not be necessary to employ a transfected cell which expressed the complete hormone molecule could alternatively be employed (i.e., a cell containing a gene fragment of the hormone molecule gene).

The possibility of using a gene fragment to induce antibody production provides a substantial advance in the art. The procedure may advantageously be employed in the cloning of genes, even when neither the gene poroduct nor the full-length gene has been isolated. The method also permits the isolation of region-specific polyclonal antibodies which are of substantial importance in immunodiagnostics and immunotherapy.

V. Uses of the Antibodies of the Present Invention

The desired gene product expressed in a transfected cell will very frequently be "antigenic" to the recipient subject (i.e., capable of inducing the expression of antibodies) unless immunosuppressive therapy is provided. A gene product is antigenic (i.e., is an antigen) if it contains an "epitope." An "epitope" is that portion of a molecule which is recognized by the recipient subject, and to which the induced antibodies of the recipient subject can bind. An antigen may be composed of one or more than one epitope.

The use of the present invention permits the production of two different types of antibody molecules: "polyclonal antibodies" and "region-specific polyclonal antibodies." "Polyclonal antibodies" are produced by a subject in response to the presence of the product of a complete (i.e. entire or natural) gene. "Region-specific polyclonal antibodies" are produced by a subject in response to the presence of a fragment of a complete gene product. For example, if the human insulin protein were expressed in an immunocompetent mouse, the mouse would produce a set of polyclonal antibodies capable of binding to the insulin epitopes. Although each particular antibody would, in general, be capable of binding to only one insulin epitope, the set would include antibodies capable of binding to each of the different insulin epitopes. In contrast, if only one-half of the human insulin protein was expressed in the mouse, the mouse would produce a set of polyclonal antibodies capable of binding only those insulin epitopes present on the expressed insulin fragment. Although such antibodies are "polyclonal antibodies" with respect to the expressed fragment, they are "region-specific polyclonal antibodies" with respect to the complete insulin molecule.

In summary, if a sample of polyclonal antibodies is capable of binding to only some of the epitopes naturally present on a complete gene product, then the antibodies are region-specific polyclonal antibodies with respect to that complete gene product. Alternatively, if all of the epitopes of an antigen can be bound by the antibodies present in the sample, then the sample contains polyclonal antibodies with respect to that antigen. In accordance with the present invention, an antibody capable of binding a complete gene product is said to be a region-specific antibody if it is derived from, or present in, antisera which contained region-specific antibodies capable of binding that complete gene product.

The transfected cells of the present invention may contain either the gene sequence of an entire antigen or a gene sequence of a fragment of an entire antigen, and, thus, may be used to produce transkaryotic recipients that produce either polyclonal antibodies or region-specific polyclonal antibodies. These antibodies may be utilized for any of the immunoassays wherein antibodies have been previously used. The region-specific polyclonal antibodies of the invention may be used in any immunoassay wherein monoclonal antibodies have been previously used. In one embodiment, the antibodies are detectably labeled, utilizing conventional labeling techniques well known to the art. Thus, the binding molecules may be radio-labeled using, for example, radioactive isotopes such as $^3$H, $^{125}$I, $^{131}$I, and $^{35}$S.

The antibodies may also be labeled using fluorescent labels, enzyme labels, free radical labels, or bacteriophage labels, using techniques known in the art.

Typical fluorescent labels include fluorescein isothiocyanate, rhodamine, phycoerythrin, phycocyanin, alphycocyanin, and Texas Red.

Suitable enzymes include alkaline phosphatase, urease, beta-galactosidase, glucose-6-phosphate dehydrogenase, malate dehydrogenase, and peroxidase.

Two principal types of enzyme immunoassays are the enzyme-linked immunosorbent assay (ELISA), and the homogeneous enzyme immunoassay, also known as enzyme-multipled immunoassay (EMIT). In the ELISA system, separations may be achieved, e.g., by use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds including luciferin, luciferase, and aequorin.

Once labeled, the binding molecule may be employed to detect, i.e., to identify and/or quantify immuno-logic counterparts utilizing techniques well-known to the art. Thus in the present invention the term "detect" includes identification of the presence of the molecule or functional group and also includes quantifying same.

A good description of a radioimmune assay (RIA) may be found in *Laboratory Techniques and Biochemistry in Molecular Biology*, by Work, T. S., et al., with particular reference to the chapter entitled "An Introduction to Radioimmune Assay and Related Techniques" by Chard, T., North Holland Publishing Company, New York, N.Y. (1978), incorporated by reference herein.

The polyclonal antibodies (and in particular the region-specific polyclonal antibodies) of the present invention may also be adapted for utilization in an immunometric assay, also known as "2-site" or "sandwich" assays. In a typical immunometric assay, a quantity of unlabeled antibody is bound to a solid support that is insoluble in the fluid being tested and a quantity of soluble antibody bearing a label that permits detection and/or quantitation of a ternary complex formed between solid phase antibody, antigen, and labeled antibody is added.

Typical immunometric assays include "forward" assays in which the antibody bound to the solid phase is first contacted with the sample being tested to extract the antigen from the sample by formation of a binary solid-phase antibody-antigen complex. After a suitable incubation period, the solid support is washed to remove the residue of the fluid sample, including unreacted antigen, if any, and then contacted with the solution containing an unknown quantity of labeled antibody. After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. These "two-site" or "sandwich" assays are described by Wide at pages 199–206 of "Radioimmune Assay Method," edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplex labeled antibody. The presence of labeled antibody associated with the solid support is then determined as it would be in a conventional "forward" sandwich assay.

In the reverse assay, stepwise addition first of a solution of labeled antibody to the fluid sample followed by the addition of unlabeled antibody bound to a solid support after suitable incubation period is utilized. After a second incubation, the solid phase is washed in conventional fashion to free it of the residue of the sample being tested and the solution of unreacted labeled antibody. The determination of labeled antibody associated with a solid support is then determined as in the simultaneous and forward assays.

As explained above, the immunometric assays for antigen require that the particular binding molecule be labeled with a "reporter molecule." These reporter molecules or labels, as identified above, are conventional and well known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like like activity in the test fluid, stability of the enzyme and its conjugate, availability and cost of the enzyme and its conjugate, and the like. Included among the enzymes used as labels in the immunometric assays of the present invention are horseradish peroxidase, alkaline phosphatase, beta-d-galactosidase, urease, glucose oxidase, glycomylase, carbonic anhydrase, acetylcholinesterase, lysozyme, malate dehydrogenase, and glucose-6-phosphate dehydrogenase. Urease is among the preferred enzyme labels, particularly because of chromogenic pH indicators which make its activity readily visible to the naked eye.

The antibodies of the present invention may be labeled using techniques well known in the art. Typical techniques are described by Kennedy, J. H., et al., *Clin. Chim. Acta* 70:1–31 (1976) and Schuurs, A. H. W. M., et al., *Clin. Chim. Acta* 81:1–40 (1977). Coupling techniques mentioned in the latter are the glutaraldehyde method, the periodate method, the dimaleimide method, the m-maleimidobenzyl-N-hydroxy-succinimide ester method. All these methods are incorporated by reference herein.

VI. The Production of the Transfected Cells of the Present Invention

A transkaryotic cell is produced through the in vitro introduction of additional genetic sequences into a cell (FIG. 1). If such sequences integrate into the chromosome of the transfected cell or are able to replicate as extrachromosomal plasmids, then the cell may acquire the permanent capacity to direct the expression of the introduced genetic sequence. Such a cell is said to be "stably transfected." Since such cells acquire the permanent capacity to express the introduced genetic sequence, it would be preferable to employ stably transfected cells in situations in which one desired to provide the recipient subject with a prolonged capacity to produce the desired or effector gene product.

It is also possible to employ transfected cells in which the desired or effector gene sequences have not integrated into the cell's chromosome or are not extrachromosomally replicated. Such cells only transiently retain the capacity to express the desired gene sequences. Cells which possess genetic sequences which will only transiently express the desired gene sequences are termed "transiently transfected." The level of such transient expression may be increased by providing additional copies of the desired or effector gene sequence to the transfected cell. Thus, although stably transfected cells are able to express the desired or effector gene sequence for a longer period of time than transiently transfected cells, both transiently and stably transfected cells are capable of expressing such sequences at substantial levels. Indeed, if the number of copies of a gene sequence which may be introduced into a cell (transient transfection) exceeds the number of copies which can be stably maintained, then the transiently transfected cells would exhibit a higher level of expression than would stably infected cells. Thus, it is preferable to employ transiently transfected cells in the subject either when one desires expression to be of short duration or when one wishes to provide a level of expression which is different from that attainable using stably transfected cells.

To obtain stably transfected cells, one can employ the technique of Wigler, M., et al., (*Cell* 11:223 (1977)). According to this technique, a suspension of DNA (containing the desired or effector gene sequences) is complexed into small precipitates using calcium phosphate. These precipitates are added to a monolayer of cells growing in a tissue culture dish at 37° C.

The desired or effector gene sequence is preferably isolated and cloned onto a plasmid prior to being incubated with the cells. It is, however, also possible to incubate the cells with an unfractionated collection of plasmids each of which contains a different gene sequence or solely with the desired or effector gene sequence. If unfractionated plasmids are used, it is desirable to screen the resulting transfected cells for a cell which contains and expresses the desired gene sequences. Such a cell would then preferably be purified from the other transfected cells by known and commonly used techniques prior to being introduced into the subject recipient. Techniques for cell culture are extensively disclosed by Freshney, R. I. (In: *Culture of Animal Cells, A Manual of Basic Technique*) (Aln R. Liss, Inc., NY, pp. 55–78 (1983)) and Lambert, K. J., et al. (In: *Animal Cell Biotechnology*, Vol. 1, Spier, R. E., et al., Eds., Academic Press, NY, pp. 86–122 (1985)), which references are hereby incorporated by reference.

In order to identify stably transfected cells, it is, in general, necessary to screen or select such cells from the total culture of transfected cells. Thus, it is desirable to co-transfect the transfected cell with a second gene sequence capable of conferring a selectable property to the cell. This second sequence may be either on a separate molecule or may be linked to the molecule having the desired gene sequences. The selectable property conferred by this second sequence may be, for example, drug resistance such as to G418, or the capacity to grow in the presence of metabolites such as hypoxanthine or 8-azaguanidine or in the absence of nucleotides such as thymidine. It is preferred to employ a transfected cell which is deficient in the expression of the thymidine kinase gene and to employ as the second, selectable gene sequence the thymidine kinase gene of the Herpes simplex virus. A transfected cell which exhibits the stable expression of the selectable property is examined to determine whether it also expresses the desired gene sequences. This examination is done by assaying for the protein product resulting from such expression. The particular assay used will, of course, vary depending upon the nature and function of the protein product.

Procedures for performing stable or transient transfection reactions are well known in the art (Pasleau, F., et al., *Gene* 38:227–232 (1985); Kopchick, J., et al., *DNA* 4:23–31 (1985); Lopata, M. A., et al., *Nucleic Acid Research* 12:5707–5717 (1984); Gynheung, A., et al., *Mol. Cell Biol.* 2:1628–1632 (1982), all of which references are hereby incorporated by reference.)

When performing transient transfection experiments it is preferable to provide between 10–50 ug of DNA containing the desired or effector genetic sequences to between $5\times10^5$–$5\times10$ cells. In stable transfection experiments, it is preferable to provide between 1–20 ug of DNA containing the desired or effector gene sequences to between $5\times10^5$–$5\times10^6$ cells. If the gene sequence which confers the selectable property is not present on the same molecule as that containing the desired gene sequence, then it must be separately provided to the cells. In such a case, it is preferable to provide between 1.0–100 ug of this genetic sequence per $5\times10^5$–$5\times10^6$ recipient cells. After transfection, it is preferable to allow the transfected cells to proliferate and to then provide between $10^5$–$10^{10}$ cells to each recipient subject. The number of cells introduced into the recipient will be determined based upon criteria such as the expression of the desired or effector gene's product, the turnover of the product, and the amount of product required for the desired degree of physiological activity.

The transfected cells of the present invention may be introduced into a recipient subject, either by introduction into the peritoneal cavity of the subject, or subdermally (i.e., subcutaneously or submuscularly), intradermally, intramuscularly, or, preferably, by the insertion of a subcapsular implant into the capsule that surrounds the kidney. Introduction may additionally be by intracranial implant, or by intrahepatic, intravenous, intraperitoneal, intrapulmonary, intraocular, intratesticular, or intrasplanchnic means. Introduction may either be accomplished by injection or by implantation (i.e., where the cells are enclosed by a material which restricts their ability to diffuse or migrate from the site of introduction). In a preferred embodiment, the implant is a renal subcapsular, or similar, implant which may be easily recovered from the recipient and studied.

The present invention may be practiced with a transkaryotic cell derived from a wide number of diverse tissues, as long as the cell is (1) capable of receiving and expressing the introduced gene sequences, and (2) being cultured in vitro and re-introduced into the recipient subject. For example, the present invention may be practiced using fibroblasts, myocytes, hepatocytes, kidney capsular cells, endothelial cells, epithelial cells of the gut, pituitary cells, etc. The invention may be practiced using either primary cells or transfected cells. Preferred cell types include mouse L cells, kidney capsular cells, and AtT-20 cells. It is, however, most preferable to employ as the transfected cell a fibroblast cell. If one desires to minimize any possible immunological reaction of the recipient subject to the transkaryotic cell, it is desirable to employ a cell from a species which is closely related to the species of the recipient subject, and it is preferable to employ a cell from the same species as the recipient subject. To avoid an immunological response it is most preferable to employ a cell which was originally obtained from the recipient subject itself. Alternatively, an immunosuppressive drug (such as, for example, dexamethasome or anti-thymocyte antisera) may be administered to the recipient subject at a dosage sufficient- to prevent or attenuate the recipient subject's rejection or destruction of the transkaryotic implant. If, alternatively, one desires to provoke an immunological response (for example, to induce production of an antibody), one could introduce a transkaryotic implant containing either stably or transiently transfected cells of either the same species or a diverse species.

Thus, the present invention begins with the in vitro cultivation of a tissue culture cell or a primary cell from an organ explant. A desired or effector gene sequence is then incubated in the presence of the cell under conditions which permit it to be adsorbed into the cell. The resulting transfected cell may then be introduced into a recipient subject by any of a variety of means. Once within the recipient subject, the transfected cell's in vitro-introduced gene sequences can then be expressed and provide the recipient subject with the desired gene product.

In the examples below, transfected cells which express human growth hormone or insulin have been employed. It is to be understood that the present invention is not limited to the use of such transfected cells, but rather encompasses the use of any transfected cell capable of expressing any gene in a recipient subject. Examples of other genes which could alternatively have been employed include genes for hormones, enzymes, antibodies, and the like.

Additionally, although the fibroblast and pituitary cells employed in the examples-below were not derived from the particular mice which served as the recipient subjects, it is alternatively possible to have employed transfected cells which are derived from the subject recipient itself. The experiments presented below indicate that several sites for implantation of genetically engineered cells are satisfactory and permit the vigorous function of such cells after their transference into the recipient subjects.

The use of human growth hormone has practical significance in that the growth of recipient subject mice receiving subcapsular implants of transfected cells were found to grow more rapidly than control mice for at least seven days post-implantation. Hence, the administration of transfected cells resulted in a physiologically significant level of expression. Such implants can be employed to promote rapid growth of newborn animals (it may be necessary to tolerize the animals to the transfected cells in order to avoid immunosuppressive therapy). Similarly, the expression of insulin was found to be physiologically significant.

Having now generally described this invention, the same will be better understood by reference to certain specific examples which are included herein for purposes of illustration only and are not intended to be limiting of the invention, unless specified.

EXAMPLE 1

Formation of Transfected Cells Containing the Human Growth Hormone Gene

A. Formation of Transiently Transfected Cells

Cultured mouse Ltk$^-$ fibroblasts were incubated with plasmid pXGH5 under conditions sufficient to permit its uptake into the fibroblast cells. Plasmid pXGH5 contains the human growth hormone gene fused to the mouse metallothionein-I (mMT-I) promoter region. This plasmid is described in co-pending U.S. patent application Ser. No. 06/896,483, and is on deposit at the American Type Culture Collection, Rockville, Md., under the Accession Number ATTC 67180. Plasmid transfection was performed according to the method of Lopata, M., et al.

B. Formation of Stably Transfected Cells

In order to produce stably transfected cells, mouse Ltk$^-$ (thymidine kinase deficient) fibroblasts were co-transfected with plasmid pXGH5 and the herpes simplex virus thymidine kinase gene, and HAT-resistant cell lines were analyzed for human growth hormone expression. Stable transfection was performed according to the method of Wigler, M., et al. (*Cell* 11:223 (1977)). One cell line found to produce human growth hormone expression was termed Ltk$^+$GH.

EXAMPLE 2

Intraperitoneal Implantation of Transiently Transfected Cells

Figure 2:
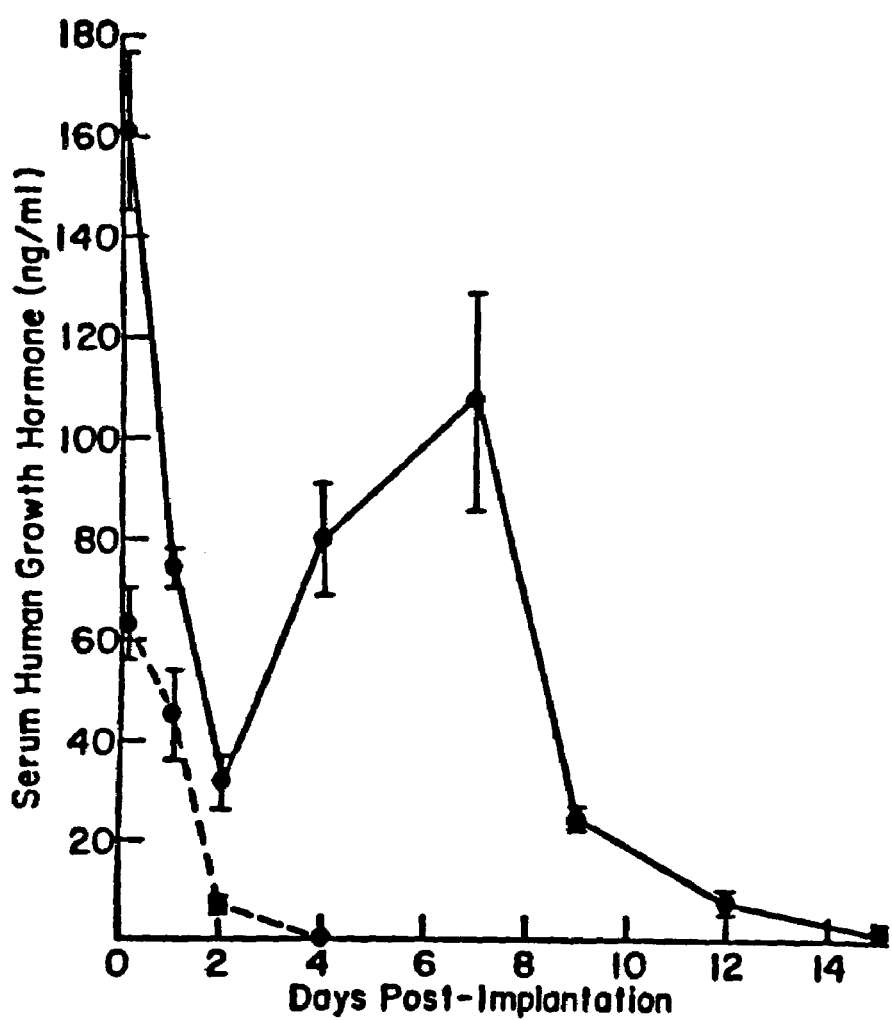
FIG. 2 shows the amount of human growth hormone detected in the bloodstream of mice which had received intraperitoneal injections of either transiently transfected (dashed lines) or stably transfected (solid lines) cells.

Transiently transfected cells were obtained as described in Example 1A. Four days after transfection with pXGH5 DNA, the recipient Ltk$^-$ cells were typsinized, pelleted, resuspended in phosphate-buffered saline, and injected intraperitoneally into a group of ten C3H mice. These mice were of the same strain as the original donor of the cultured Ltk$^-$ cell line. Approximately $2 \times 10^7$ cells were introduced into each animal. Within three hours of implantation, human growth hormone appeared in the serum of the recipient mice. The mean serum level was 63.1 mg/ml. Serum human growth hormone levels began to decline during the next day (mean level 45.1 mg/ml), and the hormone was barely detectable (mean level 0.6 mg/ml) by four days post-implantation. The results of this experiment are shown in FIG. 2 (dashed line). This experiment shows that transkaryotic implantation of transiently transfected cells can deliver a protein product to the serum of recipient mice for approximately four days post-implantation (corresponding to days 5–8 post-transfection). The implanted cells stop producing human growth hormone because the recipient has some means to remove or inactivate the cells.

EXAMPLE 3

Intraperitoneal Implantation of Stably Transfected Cells

Stably transfected cells were prepared as described in Example 1B. Cells from cell line Ltk$^+$GH were introduced intraperitoneally into a group of ten C3H mice, which were then bled for serum human growth hormone determinations at various times post-implantation. The results of this experiment are shown in FIG. 2 (solid line). The functional integrity of the implanted cells could be divided into three phases in these experiments. As with the transiently transfected cells of Example 2, serum human growth hormone was detected within three hours of implantation and declined rapidly for the next two days ("trauma phase"). Serum human growth hormone levels then increased dramatically until day 7 ("acclimation days"), and then declined to barely detectable levels by day 15 ("elimination phase").

A comparison of the implantations of transiently and stably transfected cells suggested that during the initial days after implantation, human growth hormone expression stops as a result of cell death, presumably due to a combination of the damaging effects of handling the cells and of the growth conditions in the peritoneum. The stably transfected cells recovered from this initial shock, but the transiently transfected cells did not, possibly because the manipulations involved in the transient transfection technique jeopardized the survival of cells subjected to further trauma. During the acclimation phase, the surviving cells thrive as reflected by human growth hormone production. The decline in human growth hormone levels after the seventh day was most likely due to the recipient's response to the implant rather than to an inherent inability of the transplanted cells to survive longer.

EXAMPLE 4

Figure 3:
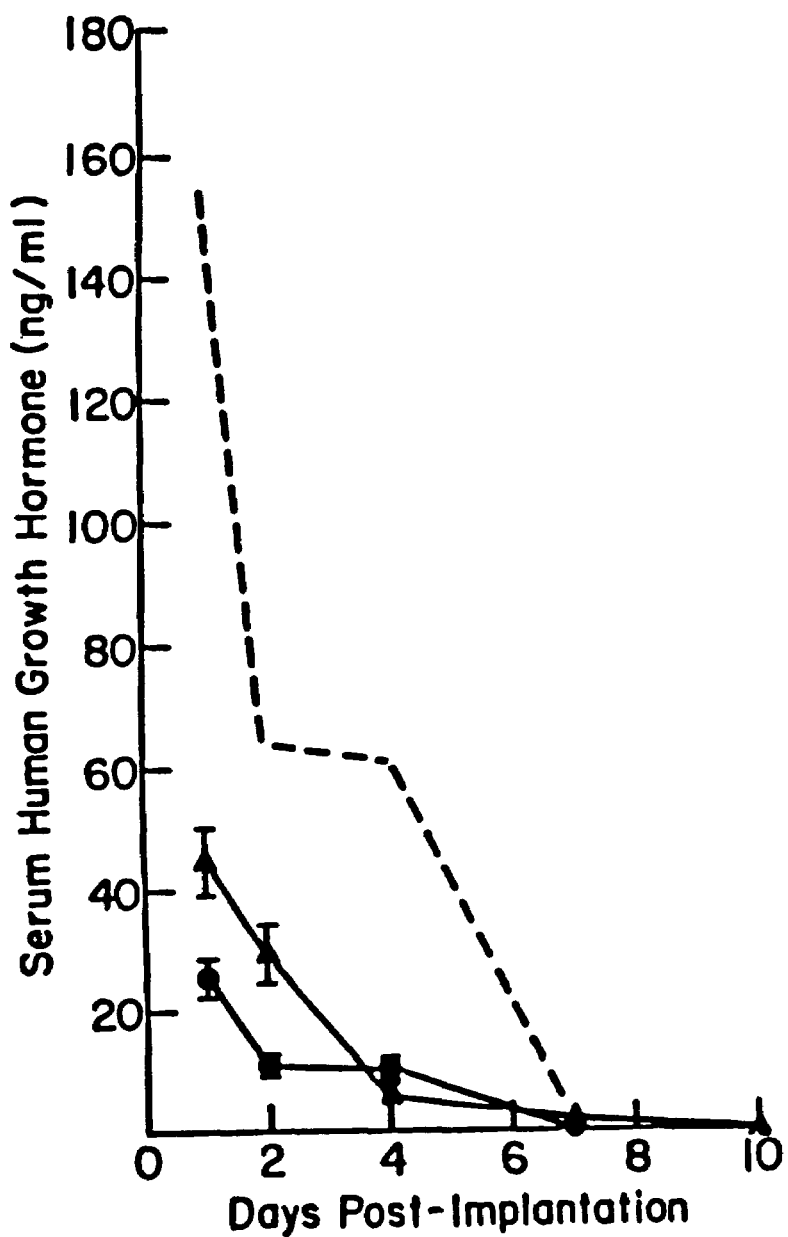
FIG. 3 shows the amount of human growth hormone present in the bloodstream of mice which had received either subcutaneous transfected cells (solid lines, triangles) or had received the transfected cells by subcapsular implantation (solid line, circles). The dashed line shows the data for subcapsular transkaryotic implants normalized to the number of cells implanted.

Effect of the Site of Implantation on the Expression and Longevity of the Transfected Cells In order to determine the effect of the site of implantation on the expression and longevity of transfected cells, stably transfected cells obtained as described in Example 1B were subcutaneously implanted into various locations in C3H mice. Approximately $2 \times 10^7$ cells were introduced per animal. The results of this experiment are shown in FIG. 3. Subcutaneously implanted transfected cells were found to produce human growth hormone for up to ten days (FIG. 3, solid line, triangles). Serum human growth hormone levels fell steadily from day one post-implantation, and the acclimation phase noted with intraperitoneal implantation was not seen with subcutaneous implantation. A similar pattern was found for cells implanted under the renal capsule (FIG. 3, solid line, circles). The dashed lines show the results for the subcapsular implants normalized to the number of cells implanted. In this experiment, $3 \times 10^6$ cells were infected into each animal. By day seven post-implantation, these implants produced little serum growth hormone. The subcutaneous implants were removed and used in histochemical studies. Cells staining positively for human growth hormone were found to have been present within the subcapsular implant, and the morphology of the renal praenchyma was found to have been normal. As a control for the role, if any, of human growth hormone and the survival of implanted cells, non-transfected Ltk$^-$ cells were also subcapsularly implanted. The fate of these cells was identical to that of the subcapsularly implanted transfected cells.

Several factors may have played a role in the differential ability of the implanted cells to produce human growth hormone in various locations in the body. The profusion of the implant site could have provided the cell with vital nutrients and influenced both the viability of the cells and the amount of human growth hormone taken up into the circulatory system. The hydrostatic pressure to which the cells were subjected could also have influenced the functioning of the implant—cells under the renal capsule, for example, are presumably under significantly higher hydrostatic pressure than those in the peritoneum. The cells may have attached better in certain locations, and finally, the relative surveillance of the implant by cells of the immune system may have influenced the amount of human growth hormone produced.

EXAMPLE 5

The State of the Implanted Cell

Figure 4:
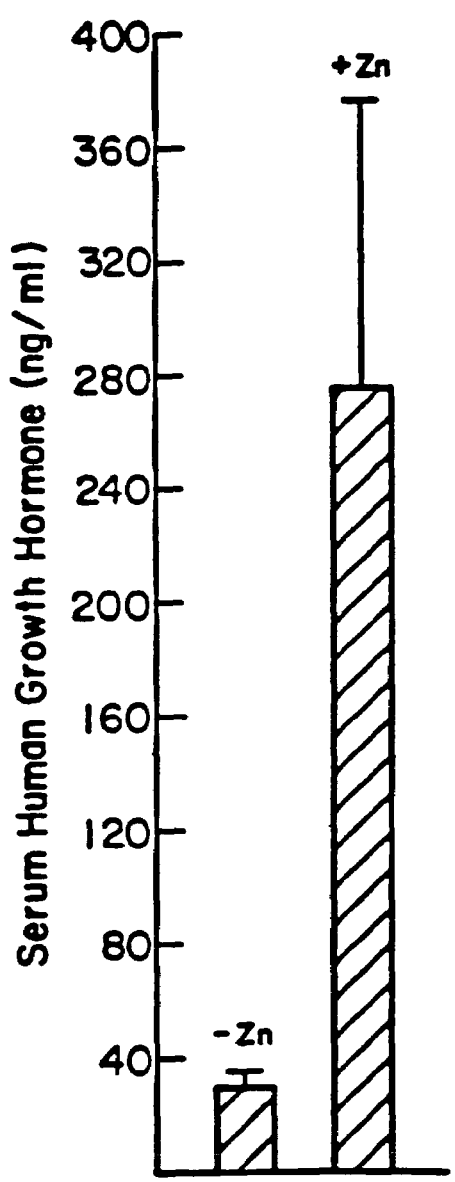
FIG. 4 shows the effect of zinc administration on the levels of growth hormone in a mouse containing transfected cells in which growth hormone gene was controlled by the metallothionein-I promoter.
Figure 5:
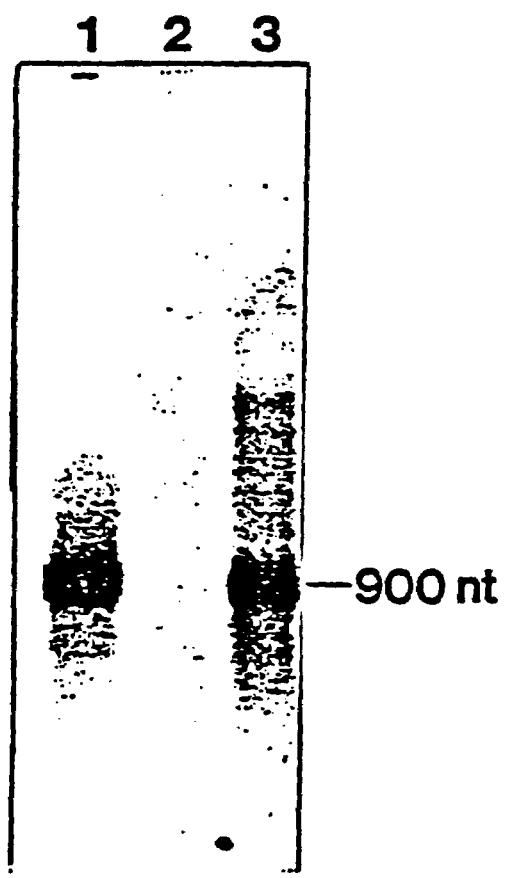
FIG. 5 shows the detection of mouse metallothionein-I/human growth hormone mRNA in transfected cells recovered from a subcapsular implant.

As described above, the plasmid pXGH5 contains the mouse metallothionein-I promoter. In order to determine whether the implanted cells were sufficiently healthy to respond to their local environment, the ability of zinc to induce higher levels of human growth hormone expression was determined. Stably transfected cells, prepared as described in Example 1B, were implanted intraperitoneally in mice, some of which were given 76 mM ZnSO$_4$ in their drinking water. The animals treated with zinc expressed ten-fold more human growth hormone in their serum than did those with no treatment. The results of this experiment are shown in FIG. 4. This induction was comparable to previously reported results for metallothionein fusion genes (Searle, P. F., et al., *Molec. Cell Biol.* 5:1480–1488 (1985); Selden, R. F., et al., *Molec. Cell. Biol.* 6:3173–179 (1986)) and indicated that the cells remained responsive in the intraperitoneal milieau. Furthermore, RNA prepared from cells recovered from subcapsular implants contained the correct mMT-I/human growth hormone fusion mRNA (FIG. 5). Taken together, these results strongly suggest that the implanted cells were healthy and behaved predictably. Of substantial importance is the fact that the cells, once in place in the animal, could still be modulated by external means. This result strongly suggests that in a clinical setting the expression of a desired or effector gene product could be modulated of pharmacologic intervention.

Whenever human growth hormone was detected in the serum of a recipient subject, it was possible to detect the presence of transfected cells. For example, from days 1 through 7 post-implantation, human growth hormone-producing cells could be visualized (either with the naked eye or by light microscopy) under the renal capsule. At the time when serum human growth hormone disappeared, the implanted cells were no longer detectable. Once human growth hormone had disappeared from the serum, it was never found to reappear. In addition, if the kidney which received the subcapsular implant was removed from a mouse expressing human growth hormone (via a transkaryotic implant), all traces of such expression disappeared within several hours after the nephrectomy. The transfected cells also appear to remain localized at the site of intraperitoneal and subcutaneous implantation. These findings indicated that the cessation of human growth hormone expression resulted from the destruction of the implanted cells.

EXAMPLE 6

Role of the Immune System in Transkaryotic Implantation

Figure 6:
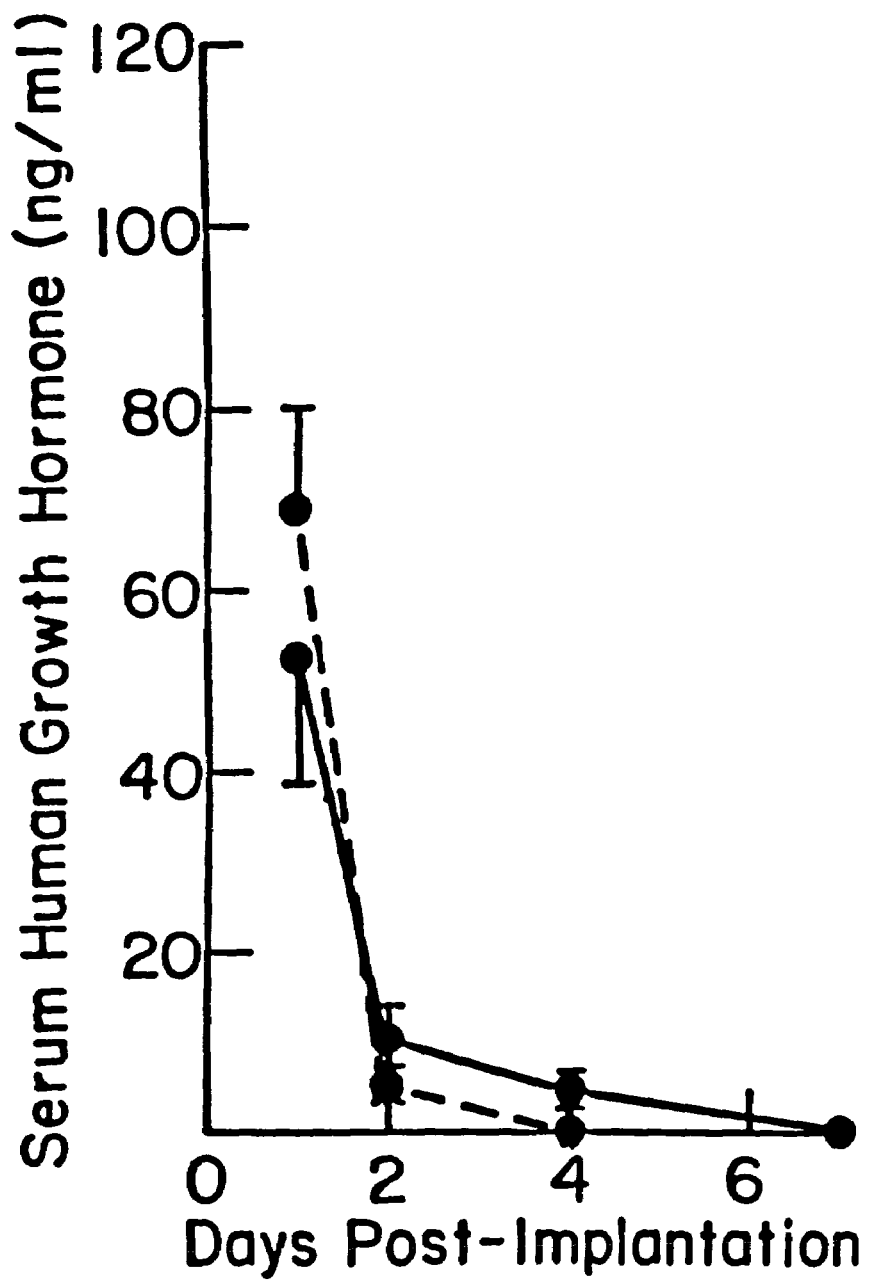
FIG. 6 shows the levels of human growth hormone as a function of the days post-implantation of stably transfected cells into a recipient mouse which had previously received a transkaryotic implant.
Figure 7:
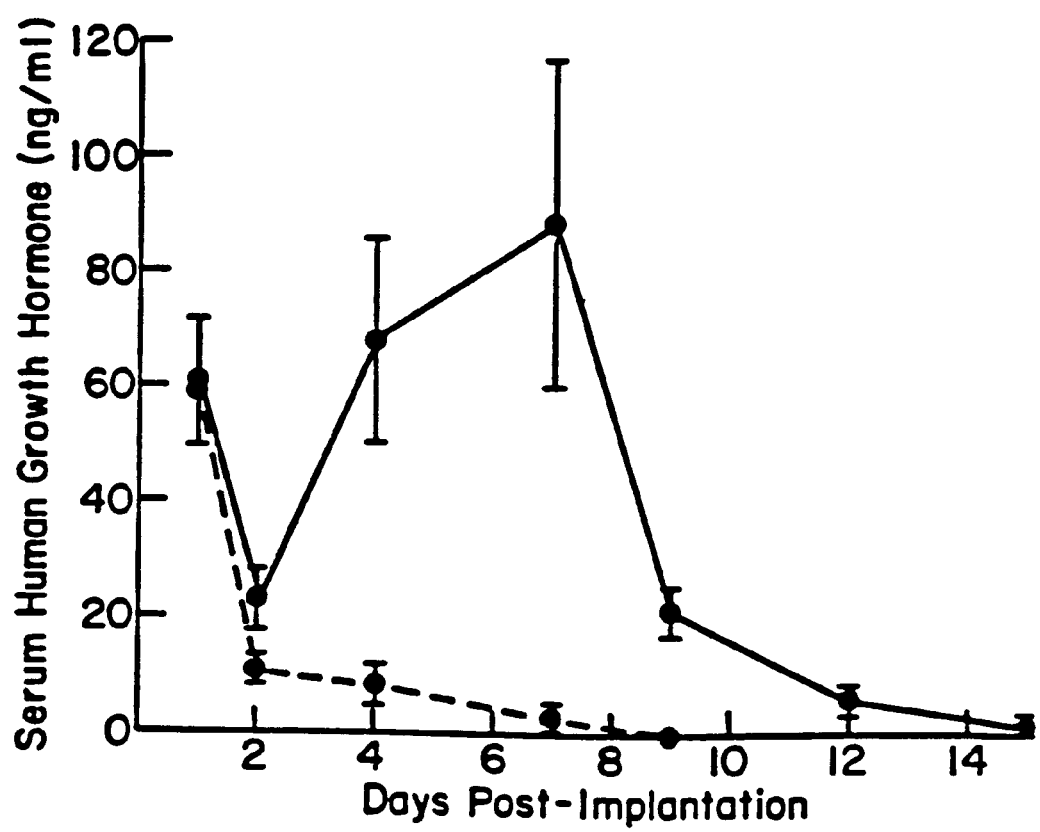
FIG. 7 shows the levels of growth hormone expressed by a a transfected implant in allogeneic mice (solid line). The dashed line shows expression of growth hormone resulting from a second subsequent implantation.

Since serum human growth hormone levels dropped precipitously between 7–15 days after intraperitoneal implantation, it seemed possible that this elimination phase was mediated by the immune system. As a first step in studying the potential role of the immune system in transkaryotic implantation, six C3H mice (of the ten mice discussed in Example 2) that had previously received intraperitoneal implants of stably transfected cells were re-challenged with stably transfected cells. When first exposed to the new transfected cells, the pattern of human growth hormone expression in these mice continued for 15 days (FIG. 6, solid lines), but after the second challenge, human growth hormone levels were barely detectable by day 7 and were absent by day 9 (FIG. 6, dashed line). The serum human growth hormone profile of the re-challenged mice also lacked the acclimation phase. These results were consistent with an anamestic response of the host mice against the transfected cells. Although the transfected cells were originally derived from C3H mice, it is likely that either the cells or the mice have undergone some genetic alteration over the course of almost four decades since the cell line was originally established, and hence, they are no longer fully syngeneic with one another. When frankly allogeneic mice (C57BL/6; representing both H-2 and non-H-2 determined incompatibilities) received transfected cells intraperitoneally, their pattern of human growth hormone expression resembled that of re-challenged C3H mice (FIG. 7, solid line). After a second challenge, no human growth hormone was detectable in the allogeneic recipients after day 4 (FIG. 7, dashed line). These experiments suggested that the primary cause of cessation of human growth hormone expression after intraperitoneal implantation was cell death due to the host's immune system.

EXAMPLE 7

Prolonging the Functional Life of the Implant

If the transfected cells are destroyed by transplant rejection, immunosuppression should prolong the functional life of the implant. In order to test this hypothesis, mice which had received stably transfected transkaryotic implants were subjected to three different immunosuppressive regimens: rabbit anti-mouse thymocite serum (Baldamus, C. A., et al., *Immunol.* 110:1532–1541 (1973), dexamethasone, and a combination of the two. Transfected cells which expressed human growth hormone were implanted intraperitoneally into C3H mice, which were then immunosuppressed and monitored for serum human growth hormone. Mice which had received anti-mouse thymocyte serum (given 0.25 ml per mouse on days −1, 1, 0, +1, and +3 with respect to implantation) showed higher serum human growth hormone levels and expressed human growth hormone for approximately two weeks longer than did untreated mice (Table I). Dexamethasone-treated mice also showed elevated and prolonged expression, with serum human growth hormone detectable until 48 days post-implantation.

TABLE I

Effects of Immunosuppression on IP Cells

| Days Post-Implantation | No Immuno-suppression | Anti-Lymphocyte Serum | Dexamethasone |
|---|---|---|---|
| 1 | 74.1 +/− 3.8 | 89.7 +/− 18.6 | 94.8 +/− 9.2 |
| 2 | 31.5 +/− 5.4 | | 86.6 +/− 10.5 |
| 3 | | 84.7 +/− 20.4 | |
| 4 | 80.0 +/− 11.4 | | 54.3 +/− 14.2 |
| 5 | | 173.1 +/− 34.6 | |
| 7 | 107.5 +/− 21.6 | 160.8 +/− 75.4 | |
| 8 to 10 | 24.3 +/− 2.1 | 38.3 +/− 5.4 | 99.3 +/− 48.0 |
| 12 to 13 | 7.4 +/− 2.1 | 28.3 +/− 5.6 | 32.0 +/− 15.1 |
| 15 to 17 | 1.5 +/− 0.7 | 28.8 +/− 7.5 | 28.3 +/− 18.1 |
| 21 | — | 13.9 +/− 3.7 | 28.0 +/− 13.6 |
| 27 | — | 10.4 +/− 6.6 | 13.9 +/− 6.9 |
| 34 | — | — | 17.3 +/− 11.7 |
| 41 | — | — | 7.5 +/− 6.1 |
| 48 | — | — | 2.7 +/− 2.2 |
| 55 | — | — | — |

For mice receiving dual immunosuppression, anti-mouse thymocyte serum and dexamethasone were administered as described above. These mice expressed human growth hormone for over three months (Table II). In approximately 20% of the group, human growth hormone levels rose to approximately 500 mg/ml. Such high levels of serum human growth hormone for an extended period often proved to be lethal to the mice—on laparotomy, large collections of transfected cells were found which formed plaques of new tissue distributed widely on many peritoneal surfaces. Viable cells were also found to be suspended in the ascites fluid.

The ultimate death of these mice was not caused by the increased peritoneal cell mass, since approximately 20% of control C3H mice which were injected with non-transfected fibroblast cells exhibited similar cell proliferation. The control mice, however, survived for over 100 days post-implantation. Thus the death of the mice which received the transkaryotic implant was probably attributable to the extremely high serum levels of growth hormone.

TABLE II

Effects of Dual Immunosuppression

| Days Post-Implantation | Intraperitoneal ALS + DEX | Subcapsular ALS + DEX |
|---|---|---|
| 1 | 9.4 +/− 2.9 | 25.8 +/− 4.5 |
| 2 | 2.9 +/− 0.8 | 11.4 +/− 1.6 |
| 4 | 5.8 +/− 1.7 | 17.5 +/− 2.2 |
| 7 | 7.5 +/− 3.6 | 19.4 +/− 2.4 |
| 10 | 9.6 +/− 3.9 | 53.4 +/− 16.2 |
| 13 | 43.7 +/− 19.3 | 26.2 +/− 7.2 |
| 16 | 22.0 +/− 8.5 | 7.5 +/− 2.1 |
| 21 | 18.3 +/− 7.5 | 6.1 +/− 1.7 |
| 28 | 14.1 +/− 5.9 | 12.2 +/− 6.5 |
| 35 | 13.1 +/− 6.9 | 9.2 +/− 2.8 |
| 42 | 9.7 +/− 4.9 | 9.7 +/− 5.0 |
| 50 | 12.2 +/− 6.4 | 7.4 +/− 4.6 |
| 58 | 8.6 +/− 4.1 | 2.7 +/− 1.8 |
| 66 | 144.2 +/− 84.4 | 4.0 +/− 2.6 |
| 73 | 132.2 +/− 105.8 | 3.7 +/− 2.4 |
| 80 | 31.7 +/− 24.0 | 3.0 +/− 2.4 |
| 87 | 16.9 +/− 13.8 | 4.0 +/− 3.3 |
| 94 | 14.0 +/− 11.5 | 6.2 +/− 4.3 |

EXAMPLE 8

Survival of Subcapsular Implants in Immunosuppressed Mice

In order to determine whether immunosuppression would lead to prolonged expression of human growth hormone by transfected cells of a subcapsular implant, mice which had received such an implant below the kidney capsule were treated with a combination of rat, anti-mouse thymocyte serum, and dexamethasone and the levels of human growth hormone expression were monitored. Serum human growth hormone levels peaked after approximately 10 days post-implantation, declined over the next six days, and then remained level at approximately 5–10 mg/ml for more than two months. Although dexamethasone was administered to these mice for one week after implantation of intraperitoneal or subcapsular cells, its effects allowed the implant to survive for several weeks after the cessation of dexamethasone administration. It is possible that the ultimate destruction of the cells was related to a dexamethasone-sensitive event that occurred soon after implantation. This event could not be the only one involved in the destruction because when C3H mice were treated continuously with dexamethasone alone, the transfected cells are eventually destroyed.

EXAMPLE 9

Production of Human Insulin by a Transkaryotic Implant

Mouse Ltk$^-$ cells were transfected with a thymidine kinase gene and a fusion gene designed to express a human preproinsulin messenger RNA. When transfected with such fusion genes, mouse Ltk$^-$ cells constitutively secrete proinsulin but are unable to produce mature insulin. One clonal line (named Ltk$^+$Ins) which contained several human insulin fusion genes, synthesized human insulin messenger RNA, and secreted human pro-insulin, was chosen for further analyses.

Figure 8:
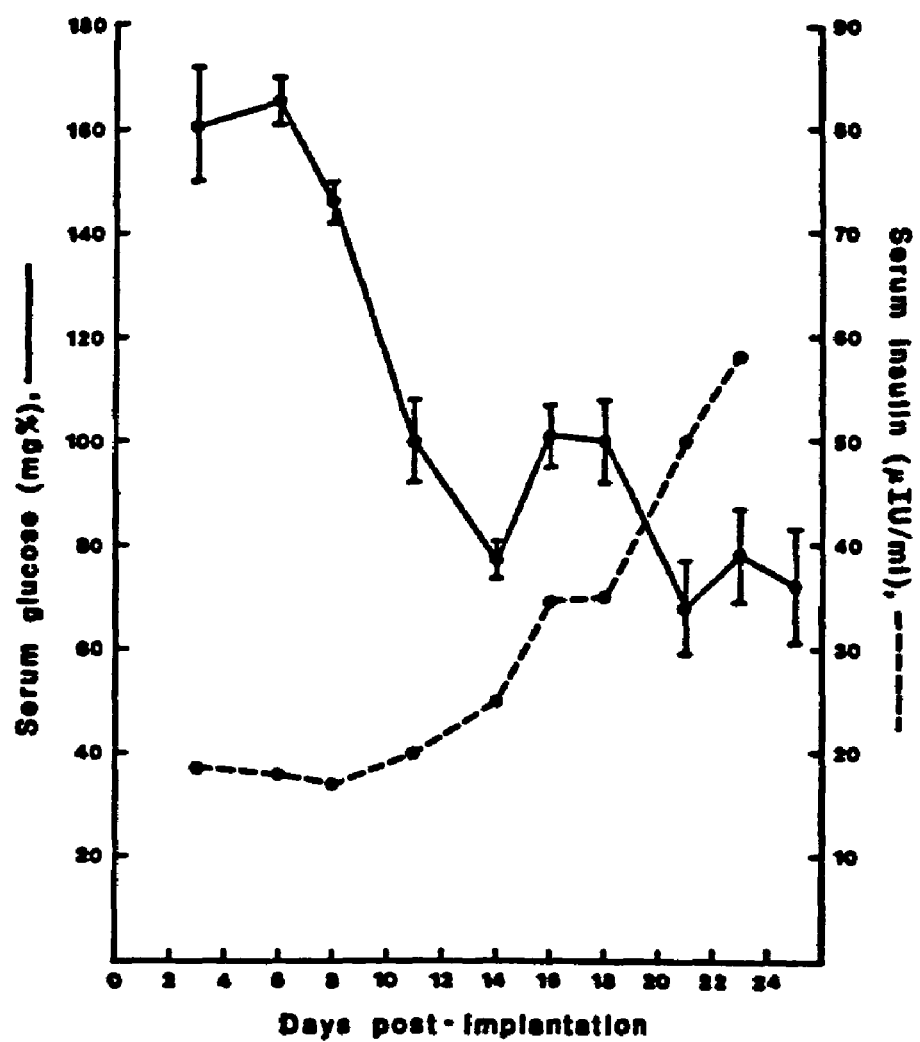
FIG. 8 shows the delivery of functional insulin genes to normal and diabetic mice using transkaryotic implantation. The Ltk$^+$Ins cell line was selected after co-transfection with a mouse metallothionien-I/human insulin fusion gene (inset). Approximately $10^7$ Ltk$^+$Ins cells were injected intraperitoneally-into ten nude mice. Mice were bled after two hour fasting on indicated days post-transfection. Serum glucose levels (solid line) were determined as recommended by the manufacturer (Worthington), and average levels and standard error bars are shown. Average serum insulin levels (dashed line) were determined by pooling serum samples from the mice and were performed as recommended by the manufacturer (Diagnostic Products).

To circumvent the need for immunosuppression, nude mice were utilized as recipients for the Ltk$^+$Ins cells. Approximately 10$^7$ cells were intraperitoneally injected into each of 10 mice, and serum samples (after two-hour fasting) were obtained two to three times weekly (FIG. 8). For almost one week post-implantation, serum glucse levels remained at pre-implantation values (160 mg %+/− standard error of 10 mg %). A precipitious fall in glucose levels was noted between weeks one and two (to 77 mg %+/−4 mg %), and the levels remained low for the duration of the experiment. In parallel with this drop in glucose levels, the total insulin levels rose markedly from preimplantation values of approximately 17 uIU/ml to almost 60 uIU/ml. Since the total insulin assay has only 20% cross-reactivity with pro-insulin, the actual proinsulin levels in these animals may be significantly higher than reflected by these measurements. These results indicate that transkaryotic implantation can be utilized to deliver functional insulin genes and reduce serum glucose levels in mice.

EXAMPLE 10

Use of Transkaryotic Implantation to Treat Diabetes

Figure 9:
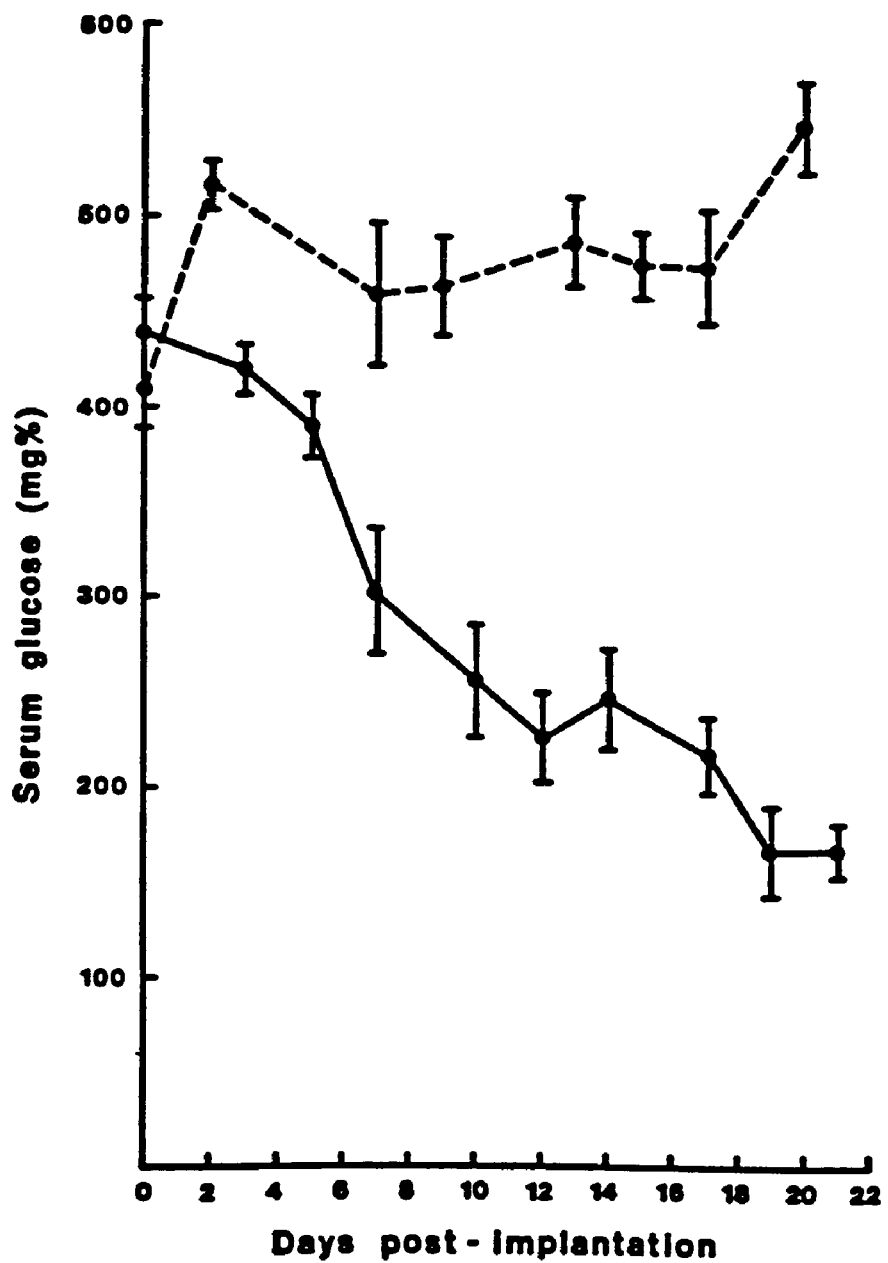
FIG. 9 shows the ability of transkaryotic implants to provide physiologically significant levels of insulin. Ten C3H mice were immunosuppressed and injected intraperitoneally as described above. Mice were bled after two hour fasting and serum glucose levels were determined. Five of the mice showed prolonged declines of serum glucose levels (solid line) and ultimately became hypoglycemic. Serum glucose levels from a group of five diabetic mice that did not undergo transkaryotic implantation were monitored as a control (dashed line).

The potential application of transkaryotic implantation to the treatment of diabetes was modelled by monitoring the effect of intraperitoneally injected Ltk$^+$Ins cells on diabetic mice. To obtain chemically diabetic animals, C3H mice were treated with streptozotocin (8 mg/mouse), and (two-hour fasting) serum glucose levels were measured approximately 10 and 15 days later. For the purposes of this study, a mouse was considered to be diabetic if its fasting serum glucose level was 400 mg % or greater, and 10 of these mice received intraperitoneal injections of Ltk$^+$Ins cells. The C3H mice were immunosuppressed using rabbit anti-mouse thymocyte serum and dexamethasone. Within one week post-implantation, a dramatic decline in serum glucose levels was noted in five of the mice (FIG. 9, solid line). By two weeks post-implantation, normoglycemia was restored in these diabetic mice. The remaining five mice showed either a transient decline in serum glucose levels or no decline at all, suggesting that immunosuppression was not equally effective for every mouse (data not shown). Control diabetic mice (FIG. 9, dashed line) showed no reduction in serum glucose levels. Serum glucose levels continued to fall in the group of five responding animals, and ultimately, these diabetic mice succumbed from transkaryotic implantation-induced hypoglycemia.

Some diseases may prove to be more tractable than diabetes, and it is possible that the search for a regimen of diabetic gene therapy may lead to treatments of conditions where tight, minute-to-minute regulation of the delivered protein is not essential. Hemophilia, for example, might be treated if the missing clotting factor could be provided by genetically engineered cells. Presumably, the requirements for the range of concentrations of the factor and the type of cell used to produce it are less rigid than those for the treatment of diabetes.

EXAMPLE 11

Use of Transkaryotic Implantation to Obtain Polyclonal Antibodies

Antibodies to human growth hormone were produced as follows: Approximately 2×10$^7$ mouse Ltk$^-$ cells were transiently transfected with pXGH5 using the DEAE-dextran transfection protocol of Selden, R., et al. (*Molec. Cell. Biol.* 6:3173–3179 (1986)). Four days after transfection, the cells were washed, trypsinized, and implanted into C3H mice intraperitoneally. This treatment was repeated after two weeks, and animals were bled weekly to obtain samples for ELISAs.

Prior to the experiment, the mice contained no detectable antibodies to human growth hormone. Within two weeks of administration of the transiently transfected cells, the anti-hGH titre (by ELISA) averaged 1600 for the five mice. Fifteen days after the first injection, the animals received a second dose of transiently transfected cells, and approximately two weeks later (i.e., day 27 after the first injection) the average titre was 38,000. All five mice produced anti-hGH antibodies, and the individual titres ranged from 12,800 up to 102,400. Unless the animals were treated with additional cells, the anti-hGH titres gradually dropped off, and, by 68 days after the first injection, they were found to be approximately 4000.

Several variations of the above-described protocol may be successfully employed. For example, stably transfected (instead of transiently transfected) cells may be used. The transfected Ltk$^-$ cells have been utilized to produce antibodies in mice, guinea pigs, and rabbits. Antibodies have also been produced to human growth hormone, the human growth hormone variant, insulin, and proinsulin cells, such as AtT-20 cells may alternatively be employed.

EXAMPLE 12

Use of AtT-20 Cells in Transkaryotic Implantation

The AtT-20 cell line is a well-characterized pituitary tumor cell line that was derived from a spontaneous tumor from a LAF1 mouse. These cells were transfected with pXGH5 (a plasmid containing the mMT-I/hGH fusion gene) and pKONEO (a plasmid containing a gene encoding resistance to the drug G418). A clonal line of stably transfected cells, termed AtT-20 (neo$^+$) F6 was chosen for further analyses. This line expressed significant amounts of hGH, and, since this cell has retained its secretory apparatus, about two-thirds of the hGH is secreted and the remaining one-third is stored in secretory granules.

Approximately $5 \times 10^6$ cells were injected intraperitoneally into LAF1 mice, and these mice were bled at approximately weekly intervals after implantation to determine serum hGH levels. During the first few days after implantation, serum hGH levels were relatively low (1–3 ng/ml). Over the course of the next month, these levels gradually rose, reaching approximately 10 ng/ml.

It is worth noting that the pattern of hGH expression using AtT-20(neo$^+$)F6 cells was quite different than that found using the Ltk$^+$GH cells (Example 11). This difference can be used to the clinician's advantage: a. Different cell types have different properties. The AtT-20 cells, for example, secrete hGH in response to cyclic AMP analogues. b. Different cell types exhibit different behaviors in the transkaryotic animal—i.e., time course, level, longevity of expression.

Similar studies have also been done with AtT-20 cells that are stably expressing human insulin. A clonal line of stably transfected cells containing pHINT5 (a mouse metallothionein-I/human insulin fusion gene) and pKONEO has been prepared. This line is called AtT-20(neo$^+$)10a and secretes properly processed insulin into the medium [in contrast, L cells transfected with pHINT5 secrete proinsulin]. When implanted intraperitoneally into nude mice, serum glucose levels decrease in much the same way as seen with the pHINT5-containing L cells, and serum human insulin levels were found to increase.

EXAMPLE 13

Production of Region-Specific Polyclonal Antibodies Through the Use of Transfected Cell Preparations Transfected cells which express the amino terminal fragment of a protein molecule are prepared as described previously, and implanted into a recipient subject. No immunosuppressive agents are provided to the recipient subject. The transfected cell expresses the amino terminal fragment of the protein. The presence of this fragment in the recipient subject induces the subject's non-transfected cells to produce polyclonal antibodies capable of specifically binding to the expressed amino terminal protein fragment. These polyclonal antibodies are region specific (i.e., capable of binding only to epitopes present on the expressed amino terminal fragment).

A gene fragment which encodes the carboxy terminal fragment of the same protein molecule as described above is isolated and used to produce a transfected cell capable of expressing the carboxy terminal fragment of the protein molecule. A preparation is prepared, using this cell, and implanted into a recipient subject. The expression of the carboxy terminal fragment by the transfected cell induces the non-transfected cells of the recipient subject to produce polyclonal antibodies capable of specifically binding to epitopes present on the carboxy terminal fragment of the expressed protein molecule. These polyclonal antibodies are region specific.

EXAMPLE 14

Polyclonal Immunoassays

The region specific polyclonal antibodies described in Example 12 may be employed in a diverse variety of immunoassays. For example, the polyclonal antibody capable of recognizing the amino terminal fragment of the protein molecule may be bound to a solid support. A sample, which possibly contains the protein molecule of Example 12 is incubated in the presence of the solid support for a time sufficient to permit any protein molecule present in the sample to bind to the bound polyclonal antibodies. The polyclonal antibodies described in Example 12 which are capable of recognizing the carboxy terminus of the protein molecule are detectably labeled and incubated in the presence of the solid support and sample. After a time sufficient to permit binding of the carboxy terminal specific polyclonal antibodies to any protein molecule present (either free in the sample or bound to the solid support), the amount of detectably labeled polyclonal antibody bound to the solid support is measured. The amount of bound carboxy terminal specific polyclonal antibody is directly proportional to the concentration of protein molecule in the sample.

As would be obvious to those of ordinary skill in the art, the above-described region-specific polyclonal antibodies may be used in a wide variety of different immunoassays (i.e., homogeneous, heterogeneous, etc.), and such use is intended to be included by the present invention. In general, any existing monoclonal antibody immunoassay may be adapted to use the polyclonal antibodies of the present invention.

EXAMPLE 15

Production of Hybridomas Using Transkaryotic Implantation

Transkaryotic cells which express a particular gene product are produced and introduced into a recipient animal by the methods of any of examples 1–4. The presence of the expressed desired gene product in the recipient animal stimulates the expression and proliferation of those antibody-producing cells which produce an antibody capable of binding to the expressed desired gene product. The splenocytes of the recipient animal are removed and cultured by procedures known in the art (see, for example, the method of Gerhard et al., *Eur. J. Immunol.* 5:720–725 (1975)). The removed splenocytes are then permitted to fuse to myeloma cells according to the method of Koprowski et al. (U.S. Pat. No. 4,172,124) or Kohler et al. (*Nature* 256:495–497 (1975)), in order to produce hybridoma cells which produce a monoclonal antibody capable of binding to the desired gene product.

The above-described method of producing hybridoma cells has several substantial advantages over methods of immunization of animals which require antigen molecules. The novel method described above does not require the initial purification of the antigen molecule, thus permitting its use in those situations in which such purification is not practical.

The above-described method may be used to facilitate the screening of resultant hybridoma cells for those which produce desired monoclonal antibodies. In conventional hybridoma technology, the hybridoma cells produced must be screened in order to identify those which produce antibody against a desired epitope. Such screening may be avoided in the present invention by introducing into the recipient animal transkaryotic cells which contain only a fragment of the antigen gene (and thus, are capable of producing only a fragment of the antigen molecule). By preselecting the gene fragment which is to be expressed by the transkaroytic cell, it is possible to limit the diversity of the hybridoma population.

EXAMPLE 16

Use of Transkaryotic Implantation to Identify Immunosuppressive Agents

If, in a transkaryotic implantation experiment, the implanted cells and the host animals are not syngeneic, the immunocompetent host will cause the rejection of the implanted cells. This rejection can be monitored by assaying for a product of the implanted cells, preferably hGH. When the transkaryotic animal is immunosuppressed, however, this rejection will be delayed or prevented, depending on the efficacy of the immunosuppressive regimen. In other words, the immunosuppressive regimen can be quantitatively evaluated by monitoring the levels and duration of serum hGH expression. Using this approach, several immunosuppressive agents have been studied, including cyclosporin, cyclophosphamide, dexamethasone, rabbit anti-mouse thymocyte antiserum, and anti-mouse thymocyte monoclonal antibodies. This technique is a straightforward, quantitative alternative to current methods of evaluation of immunosuppression.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as as follows in the scope of the appended claims.

What is claimed is:

1. A method of transferring a plasmid containing a DNA sequence coding for a protein into a recipient subject comprising:
    (a) transfecting autologous somatic cells in vitro with a plasmid containing a DNA sequence coding for a protein and which comprises a promoter by chemical or physical techniques to introduce the plasmid containing a DNA sequence coding for a protein into the cells;
    (b) screening the resulting transfected somatic cells in vitro to select a cell, wherein the selected cell is stably transfected with the plasmid containing a DNA sequence coding for a protein so that the selected cell has the permanent capacity to direct expression of the DNA sequence coding for a protein; and
    (c) cloning and expanding the selected somatic cell in vitro; and
    (d) injecting the resulting transfected, isolated, autologous, screened, cloned, and expanded somatic cells into the recipient subject.

2. The method of claim 1, wherein the somatic cells are human cells.

3. The method of claim 2, wherein the human cells are selected from the group consisting of fibroblasts, myocytes, hepatocytes, kidney capsular cells, endothelial cells, epithelial cells of the gut, and pituitary cells.

4. The method of claim 2, wherein the plasmid contains a DNA sequence coding for a hormone or an enzyme.

5. The method of claim 2, wherein the plasmid contains a DNA sequence coding for human growth hormone.

6. The method of claim 2, wherein the plasmid contains a DNA sequence coding for human insulin.

7. The method of claim 2, wherein the transfection comprises calcium phosphate-mediated transfection, microinjection, electroporation, or DEAE-dextran transfection.

8. The method of claim 2, wherein the plasmid further comprises a regulatable promoter.

9. The method of claim 8, wherein the plasmid further comprises a selectable gene, and wherein the promoter is operably linked to the selectable gene.

10. The method of claim 2, wherein the screening step further comprises screening the resulting transfected somatic cells in vitro to select a cell possessing desired expression properties.

11. A method of transferring a plasmid containing a DNA sequence coding for a protein into a recipient subject comprising:
    (a) providing autologous somatic cells;
    (b) transfecting the somatic cells in vitro with a plasmid containing a DNA sequence coding for a protein and further comprising a promoter capable of functioning in the somatic cells, wherein the somatic cells are stably transfected with the plasmid containing a DNA sequence coding for a protein so that the somatic cells have the permanent capacity to direct expression of the DNA sequence coding for a protein upon induction of the promoter;
    (c) screening the resulting transfected somatic cells in vitro to select a transfected somatic cell, wherein the screening comprises characterizing the transfected somatic cell with respect to expression and regulation of the DNA sequence coding for a protein by assaying for translation of mRNA into protein;
    (d) cloning and expanding, in vitro, the transfected and screened somatic cell selected in step (c) to form the $10^5$–$10^{10}$ transfected, screened, cloned, and expanded somatic cells,
    (e) combining the $10^5$–$10^{10}$ transfected, screened, cloned, and expanded somatic cells with a physiologically acceptable buffer or carrier; and
    (f) injecting the resulting transfected, isolated, autologous screened, cloned, and expanded cell preparation into the recipient subject.

12. The method of any one of claims 2 or 11, wherein the transferred plasmid contains a DNA sequence coding for human growth hormone.

13. The method of any one of claims 2 or 11, wherein the transferred plasmid contains a DNA sequence coding for insulin.

14. The method of any one of claims 2 or 11, wherein the plasmid containing a DNA sequence coding for a protein integrates into the chromosome of the selected cell.

15. The method of any one of claims 2 or 11, wherein the plasmid containing a DNA sequence coding for a protein replicates as an extrachromosomal plasmid.

* * * * *

UNITED STATES PATENT AND TRADEMARK OFFICE
CERTIFICATE OF CORRECTION

PATENT NO. : 7,094,400 B1 Page 1 of 1
APPLICATION NO. : 08/465596
DATED : August 22, 2006
INVENTOR(S) : Richard F. Selden It is certified that error appears in the above-identified patent and that said Letters Patent is hereby corrected as shown below:

Col. 28, Claim 11, section f, line 51, "autologous" should read -- autologous, --.

Signed and Sealed this

Twenty-sixth Day of December, 2006

JON W. DUDAS
*Director of the United States Patent and Trademark Office*